(12) United States Patent
Jashek et al.

(10) Patent No.: US 12,109,407 B2
(45) Date of Patent: Oct. 8, 2024

(54) ELECTRODE PATCH

(71) Applicant: THERANICA BIO-ELECTRONICS LTD., Netanya (IL)

(72) Inventors: Ronen Jashek, Shoham (IL); Alon Ironi, Haifa (IL); Roy Zimmerman, Givatayim (IL); Ofer Rivkind, Modi'in (IL); Rostislav Barabash, Haifa (IL); Arie Ravid, Zikhron-Yaakov (IL)

(73) Assignee: THERANICA BIO-ELECTRONICS LTD., Netanya (IL)

( * ) Notice: Subject to any disclaimer, the term of this patent is extended or adjusted under 35 U.S.C. 154(b) by 997 days.

(21) Appl. No.: 16/961,110

(22) PCT Filed: Jan. 10, 2019

(86) PCT No.: PCT/IL2019/050045
§ 371 (c)(1),
(2) Date: Jul. 9, 2020

(87) PCT Pub. No.: WO2019/138407
PCT Pub. Date: Jul. 18, 2019

(65) Prior Publication Data
US 2021/0052884 A1    Feb. 25, 2021

Related U.S. Application Data

(60) Provisional application No. 62/636,306, filed on Feb. 28, 2018, provisional application No. 62/616,029, filed on Jan. 11, 2018.

(51) Int. Cl.
*A61N 1/04* (2006.01)
*A61N 1/36* (2006.01)

(52) U.S. Cl.
CPC ......... *A61N 1/0492* (2013.01); *A61N 1/0456* (2013.01); *A61N 1/36021* (2013.01); *A61N 1/36178* (2013.01)

(58) Field of Classification Search
CPC ................ A61N 1/0492; A61N 1/0456; A61N 1/36021; A61N 1/36178
See application file for complete search history.

(56) References Cited

U.S. PATENT DOCUMENTS

| 4,989,605 A | 2/1991 | Rossen |
| 6,377,848 B1 | 4/2002 | Garde et al. |

(Continued)

FOREIGN PATENT DOCUMENTS

| CN | 102946939 A | 2/2013 |
| CN | 103796715 A | 5/2014 |

(Continued)

OTHER PUBLICATIONS

English Translation of Office Action dated Jan. 10, 2023 from the Japanese patent Office in JP Application No. 2020-538104.

(Continued)

*Primary Examiner* — James M Kish
*Assistant Examiner* — Laura Hodge
(74) *Attorney, Agent, or Firm* — Sughrue Mion, PLLC

(57) ABSTRACT

Apparatus (20) is provided that includes a battery (48) including first and second poles (78, 79); and a circuit board (50) that includes electronic circuitry (53), the second pole (79) electrically coupled to the circuitry (53). A battery-isolation tab (42, 142) is removably disposed between the first pole (78) and the circuitry (53), and includes a non-conductive substrate (90) configured to electrically isolate the first pole (78) from the circuitry (53), while the tab (42, 142) is disposed between the first pole (78) and the circuitry (53); and a conductive layer (92) disposed upon the non-conductive substrate (90), the conductive layer (92) being electrically coupled to the first pole (78) and configured to facilitate electrical coupling of the first pole (78) to the circuitry (53), while the tab (42, 142) is disposed between (Continued)

the first pole (78) and the circuitry (53). Other embodiments are also described.

18 Claims, 9 Drawing Sheets

(56) References Cited

U.S. PATENT DOCUMENTS

| | | | |
|---|---|---|---|
| 6,389,143 | B1 | 5/2002 | Leedom et al. |
| 7,139,615 | B2 | 11/2006 | Solosko et al. |
| 7,729,784 | B2 | 6/2010 | Mills et al. |
| 8,795,865 | B2 | 8/2014 | Park |
| 8,983,594 | B2 | 3/2015 | Saar et al. |
| 9,002,473 | B2 | 4/2015 | Powers et al. |
| 9,333,334 | B2 | 5/2016 | Jeffery et al. |
| 9,687,652 | B2 | 6/2017 | Franke et al. |
| 10,226,615 | B2 | 3/2019 | Lang et al. |
| 10,232,166 | B2 | 3/2019 | Kanemoto et al. |
| 2005/0118497 | A1 | 6/2005 | Breen |
| 2007/0038281 | A1 | 2/2007 | Jonsen |
| 2007/0060975 | A1* | 3/2007 | Mannheimer ............ A61N 1/20 607/46 |
| 2011/0245648 | A1 | 10/2011 | Hudson |
| 2012/0021641 | A1* | 1/2012 | Briant .................. H01R 12/707 439/571 |
| 2012/0134135 | A1 | 5/2012 | Richmond |
| 2014/0249601 | A1 | 9/2014 | Bachinski et al. |
| 2014/0296934 | A1* | 10/2014 | Gozani .................. A61B 5/486 607/46 |
| 2015/0335877 | A1 | 11/2015 | Jeffery et al. |
| 2015/0352357 | A1 | 12/2015 | Wei et al. |
| 2017/0170446 | A1 | 6/2017 | Tompkins et al. |
| 2017/0197077 | A1 | 7/2017 | Harpak et al. |
| 2017/0340884 | A1 | 11/2017 | Franke et al. |

FOREIGN PATENT DOCUMENTS

| | | |
|---|---|---|
| CN | 105073187 A | 11/2015 |
| EP | 2730311 | 5/2014 |
| JP | 2000-24123 A | 1/2000 |
| JP | 2001-95928 A | 4/2001 |
| JP | 2002-521889 A | 7/2002 |
| JP | 2005-501641 A | 1/2005 |
| JP | 2005-507276 A | 3/2005 |
| JP | 2005-224387 A | 8/2005 |
| JP | 2007-507273 A | 3/2007 |
| JP | 2008-517692 A | 5/2008 |
| JP | 2008-272023 A | 11/2008 |
| JP | 2012-513876 A | 6/2012 |
| JP | 2016-106914 A | 6/2016 |
| JP | 2017-510330 A | 4/2017 |
| JP | 2017-519552 A | 7/2017 |
| JP | 2017-522127 A | 8/2017 |
| KR | 10-2009-0104584 A | 10/2009 |
| TW | M375260 U | 3/2010 |
| WO | 2008/128215 | 10/2008 |
| WO | 2011/139779 A1 | 11/2011 |
| WO | 2012/103519 A2 | 8/2012 |
| WO | 2016/113661 | 7/2016 |
| WO | 2017/051412 | 3/2017 |
| WO | 2018/060997 | 4/2018 |
| WO | 2018/215879 | 11/2018 |

OTHER PUBLICATIONS

Notice of Reasons for Rejection Translation dated Oct. 17, 2023 issued by the Japanese Patent Office in application No. 2020-538104.
An International Search Report and a Written Opinion both dated Aug. 27, 2019, which issued during the prosecution of Applicant's PCTIL2019050045.
"Axelgaard UltraStim Electrodes Catalogue." Axelgaard Manufacturing Co., Ltd. | Manufacturer of Electrodes and Hydrogel, www.axelgaard.com/Products/Electrodes/UltraStim/Snap. Accessed Jan. 1, 2019.
U.S. Appl. No. 62/636,306, filed Feb. 28, 2018.
U.S. Appl. No. 62/616,029, filed Jan. 11, 2018.
European Office Action dated Apr. 19, 2024 in Application No. 19 701 275.0.
Chinese Office Action dated Jan. 12, 2024 in Application No. 201980017110.X.

* cited by examiner

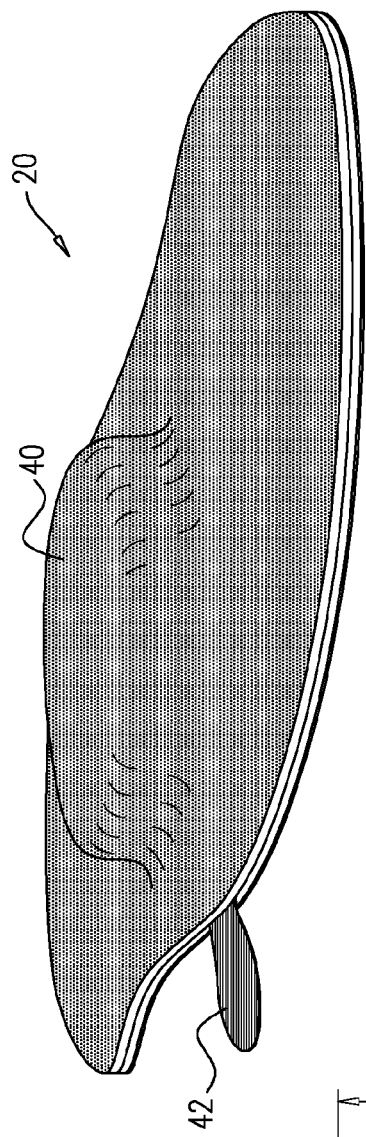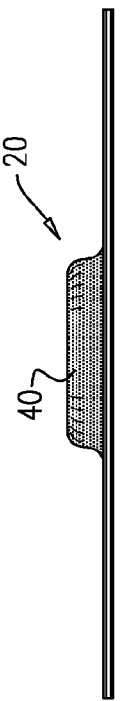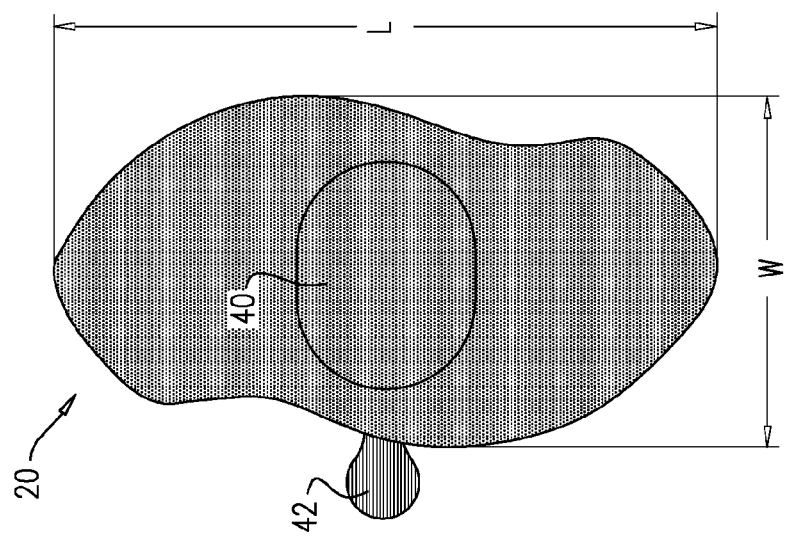

ELECTRODE PATCH

CROSS-REFERENCE TO RELATED APPLICATIONS

The present application is the U.S. national stage of International Application PCT/IL2019/050045, filed Jan. 10, 2019, which claims priority from (a) U.S. Provisional Application No. 62/616,029 to Jashek et al., filed Jan. 11, 2018, and (b) U.S. Provisional Application No. 62/636,306 to Jashek et al., filed Feb. 28, 2018, both of which are assigned to the assignee of the present application and incorporated herein by reference.

FIELD OF THE INVENTION

Some applications of the present invention generally relate to medical apparatus and methods. Specifically, some applications of the present invention relate to apparatus and methods for electrical stimulation of a subject's body.

BACKGROUND

Electrical nerve stimulation has been used as a possible treatment for acute pain relief, including headaches. Clinical studies have shown that two ranges of pulse frequencies (high frequency and low frequency) are especially effective for pain relief. Neuromodulation is a term used to describe electrical nerve stimulation when it is applied for the purpose of pain relief. Some neuromodulation techniques rely upon invasive, implantable electrical stimulation for pain relief, and others apply non-invasive stimulation via the skin.

Electromyography (EMG) is a known method used for recording of the neural-electrical activity of the skeletal muscles. Surface EMG (sEMG) uses electrode patches that are attached to the skin above the muscle of interest while its electrical potential is recorded.

SUMMARY OF THE APPLICATION

In accordance with some applications of the present invention, an electrode patch is provided that comprises a battery comprising first and second poles, and a circuit board that comprises electronic circuitry. For some applications, the second pole of the battery is electrically coupled to the electronic circuitry, and a battery-isolation tab is removably disposed between the first pole and the electronic circuitry. The battery-isolation tab is configured to electrically separate the battery from the electronic circuitry, such that the battery does not drain prior to use of the patch.

The battery-isolation tab comprises a non-conductive substrate configured to electrically isolate the first pole from the circuitry while the battery-isolation tab is disposed between the first pole and the circuitry, and a conductive layer disposed upon the non-conductive substrate. Typically, the conductive layer is electrically coupled to the first pole of the battery and configured to facilitate electrical coupling of the first pole of the battery to the circuitry while the battery-isolation tab is disposed between the first pole and the circuitry. For example, during manufacture of the electrode patch, in order to test the functionality of the electronic circuitry, or a different portion of the patch (e.g., the connectivity of electrodes of the patch), an electrical connecting element may be used to electrically couple the conductive layer of the battery-isolation tab to the electronic circuitry. Subsequently, the electrical connecting element is removed, such that the first pole of the battery is again isolated from the electronic circuitry, until the patch is ready for use. At a further subsequent time, when the patch is ready to be used by a patient, the battery-isolation tab is permanently removed, such that the first pole of the battery is directly connected to the circuitry.

For some applications, the patch comprises a battery housing configured to house the battery, such that the first pole of the battery is in contact with at least a portion of the circuit board. Typically, the battery housing comprises mechanical connectors configured to mechanically connect the housing to the circuit board, and electrical connectors configured to electrically couple the second pole of the battery to the circuit board. For some applications, the mechanical connectors and electrical connectors of the battery housing are coupled to each other, such that, by virtue of the mechanical connectors connecting the battery housing to the circuit board, the electrical connectors electrically couple the pole of the battery to the circuit board.

Typically, the patch comprises skin-contacting electrodes configured to come into electrical contact with skin of a subject, as well as a hydrogel layer underneath the skin-contacting electrodes, the hydrogel layer being configured to adhere the patch to the subject's skin. For some applications, the patch comprises a set of current-outputting electrodes disposed between the circuit board and the skin-contacting electrodes, and a set of current-receiving electrodes disposed between the circuit board and the skin-contacting electrodes. The circuit board is configured to test a connectivity of the skin-contacting electrodes, without driving any current through the hydrogel layer, by driving a test current into the skin-contacting electrodes via the current-outputting electrodes, and detecting that the outputted current is received by the current-receiving electrodes. In this manner, the connectivity of the skin-contacting electrodes is tested without interfering with (e.g., soiling, perforating, or otherwise damaging) the hydrogel layer.

For some applications, the apparatus and methods described herein are used to treat a migraine, a headache, fibromyalgia, dysmenorrhea, post-traumatic headache, premenstrual syndrome, menstrual cramps, and/or another form of pain, for example, generally in accordance with techniques described in US Patent Application Publication 2017/0368344 to Ironi et al., which is incorporated herein by reference. Typically, in response to the subject experiencing pain (such as a migraine, a headache, fibromyalgia, dysmenorrhea, post-traumatic headache, premenstrual syndrome, menstrual cramps, and/or another form of pain) in a first anatomical region, electrodes are placed on a second anatomical region of the subject body (which is a different from the first anatomical region). Electrical energy is applied to the second anatomical region by driving electrical pulses into the second anatomical region. For some applications, the electrodes are placed at location that is at a distance of more than 25 cm from the location at which the subject is experiencing pain, and the electrical energy is applied the location at which the electrodes are placed. Typically, by applying electrical energy at the second anatomical region, pain at the first anatomical region is reduced via the conditioned pain modulation mechanism.

In accordance with some applications of the present invention, a current is driven into a portion of the subject's body via the first and second electrodes, in accordance with the following stimulation protocol. The current is driven into the portion of the subject's body during a plurality of alternating current cycles, each of the current cycles containing a positive portion and a negative portion, and every N cycles, a direction in which the current cycle is driven between the first and second electrodes is reversed. Typically, N is an integer between 1 and 10. In other words, every N cycles, the order in which the positive portion and the negative portion of the current cycles are driven is reversed.

There is therefore provided, in accordance with an Inventive concept 1 of the present invention, apparatus including:
a battery including first and second poles;
a circuit board that includes electronic circuitry, the second pole of the battery being electrically coupled to the electronic circuitry; and
a battery-isolation tab removably disposed between the first pole and the electronic circuitry, the battery-isolation tab including:
a non-conductive substrate configured to electrically isolate the first pole from the electronic circuitry, while the battery-isolation tab is disposed between the first pole and the electronic circuitry; and
a conductive layer disposed upon the non-conductive substrate, the conductive layer being electrically coupled to the first pole of the battery and configured to facilitate electrical coupling of the first pole of the battery to the electronic circuitry, while the battery-isolation tab is disposed between the first pole and the electronic circuitry,
wherein the apparatus is configured such that the first pole of the battery is in electrical contact with the electronic circuitry of the circuit board, while the battery-isolation tab is not disposed between the first pole and the electronic circuitry.

Inventive concept 2. The apparatus according to Inventive concept 1, further including an electrical connecting element configured to electrically couple the conductive layer of the battery-isolation tab to the electronic circuitry, thereby electrically coupling the first pole of the battery to the electronic circuitry.

Inventive concept 3. The apparatus according to Inventive concept 2,
wherein the apparatus is configured such that the first pole of the battery is in electrical contact with the electronic circuitry of the circuit board via an electrical connection on the electronic circuitry, while the battery-isolation tab is not disposed between the first pole and the electronic circuitry, and
wherein the electrical connecting element is configured to electrically couple the conductive layer of the battery-isolation tab to a test point on the electronic circuitry, the test point electrically coupled to the electrical connection.

Inventive concept 4. The apparatus according to Inventive concept 1,
wherein the conductive layer is an upper conductive layer disposed on at least a portion of a top surface of the non-conductive substrate,
wherein the battery-isolation tab further includes a lower conductive layer disposed on at least a portion of a bottom surface of the non-conductive substrate, such that the non-conductive substrate electrically isolates the upper conductive layer and the lower conductive layer from each other,
wherein the lower conductive layer is electrically coupled to the electronic circuitry, while the battery-isolation tab is disposed between the first pole and the electronic circuitry, and
wherein the upper and the lower conductive layers are together configured to facilitate electrical coupling of the first pole of the battery to the electronic circuitry, while the battery-isolation tab is disposed between the first pole and the electronic circuitry.

Inventive concept 5. The apparatus according to Inventive concept 4, further including an electrical connecting element configured to electrically couple the upper conductive layer to the lower conductive layer, thereby electrically coupling the first pole of the battery to the electronic circuitry.

Inventive concept 6. The apparatus according to Inventive concept 1 or Inventive concept 2, wherein the conductive layer includes a printed conductive layer that is printed upon the non-conductive substrate.

Inventive concept 7. The apparatus according to Inventive concept 1 or Inventive concept 2, wherein the apparatus further includes electrodes, which are configured to be adhered to skin of a subject, wherein the electronic circuitry is configured to drive the electrodes to drive a current into the subject's skin.

Inventive concept 8. The apparatus according to Inventive concept 1 or Inventive concept 2, wherein the apparatus further includes a battery housing configured to house the battery, such that the second pole of the battery is in contact with at least a portion of the electronic circuitry, the battery housing including:
mechanical connectors configured to mechanically connect the battery housing to the circuit board; and
electrical connectors configured to electrically couple the second pole of the battery to the electronic circuitry,
the mechanical connectors and electrical connectors of the battery housing being coupled to each other, such that by virtue of the mechanical connectors connecting the battery housing to the circuit board, the electrical connectors electrically couple the second pole of the battery to the electronic circuitry.

Inventive concept 9. The apparatus according to Inventive concept 8, wherein the circuit board is shaped to define slots, and wherein the mechanical connectors include protrusions that are configured to click into respective slots of the circuit board.

Inventive concept 10. The apparatus according to Inventive concept 8, wherein the second pole of the battery is not electrically coupled to the electronic circuitry using any additional electrical coupling elements other than the electrical connectors.

There is further provided, in accordance with an Inventive concept 11 of the present invention, a method for manufacturing an apparatus, the method including:
assembling a battery, which includes first and second poles, with a circuit board that includes electronic circuitry, such that (a) the second pole of the battery is electrically coupled to the electronic circuitry, and (b) a battery-isolation tab is removably disposed between the first pole and the electronic circuitry, such that a non-conductive substrate of the battery-isolation tab electrically isolates the first pole from the electronic circuitry;
while the battery-isolation tab is removably disposed between the first pole and the electronic circuitry, temporarily electrically coupling the first pole of the battery to the electronic circuitry via a conductive layer that is (a) disposed upon the non-conductive substrate of the battery-isolation tab and (b) electrically coupled to the first pole of the battery; and
while the first pole of the battery is temporarily electrically coupled to the electronic circuitry, testing functionality of the electronic circuitry,
wherein the apparatus is configured such that the first pole of the battery is in electrical contact with the electronic circuitry of the circuit board upon removal of the battery-isolation tab from between the first pole and the electronic circuitry after manufacturing of the apparatus.

Inventive concept 12. The method according to Inventive concept 11, wherein electrically coupling the first pole of the battery to the electronic circuitry includes using an electrical connecting element to electrically couple the conductive layer of the battery-isolation tab to the electronic circuitry, thereby electrically coupling the first pole of the battery to the electronic circuitry.

Inventive concept 13. The method according to Inventive concept 12, wherein the apparatus is configured such that the first pole of the battery is in electrical contact with the electronic circuitry of the circuit board via an electrical connection on the electronic circuitry, while the battery-isolation tab is not disposed between the first pole and the electronic circuitry, and wherein using the electrical connecting element to electrically couple the conductive layer of the battery-isolation tab to the electronic circuitry including using the electrical connecting element to electrically couple the conductive layer of the battery-isolation tab to a test point on the electronic circuitry, the test point electrically coupled to the electrical connection.

Inventive concept 14. The method according to Inventive concept 11, wherein the conductive layer is an upper conductive layer disposed on at least a portion of a top surface of the non-conductive substrate, wherein the battery-isolation tab further includes a lower conductive layer disposed on at least a portion of a bottom surface of the non-conductive substrate, such that the non-conductive substrate electrically isolates the upper conductive layer and the lower conductive layer from each other, wherein the lower conductive layer is electrically coupled to the electronic circuitry, while the battery-isolation tab is disposed between the first pole and the electronic circuitry, and wherein temporarily electrically coupling the first pole of the battery to the electronic circuitry includes wherein temporarily electrically coupling the first pole of the battery to the electronic circuitry via the upper and the lower conductive layers.

Inventive concept 15. The method according to Inventive concept 14, wherein electrically coupling the first pole of the battery to the electronic circuitry includes using an electrical connecting element to electrically couple the upper conductive layer to the lower conductive layer, thereby electrically coupling the first pole of the battery to the electronic circuitry.

Inventive concept 16. The method according to Inventive concept 11 or Inventive concept 12, wherein the conductive layer includes a printed conductive layer that is printed upon the non-conductive substrate.

Inventive concept 17. The method according to Inventive concept 11 or Inventive concept 12, wherein the apparatus further includes electrodes, which are configured to be adhered to skin of a subject, wherein the electronic circuitry is configured to drive the electrodes to drive a current into the subject's skin.

Inventive concept 18. The method according to Inventive concept 11 or Inventive concept 12, wherein the apparatus further includes a battery housing configured to house the battery, such that the second pole of the battery is in contact with at least a portion of the electronic circuitry, the battery housing including:

mechanical connectors configured to mechanically connect the battery housing to the circuit board; and electrical connectors configured to electrically couple the second pole of the battery to the electronic circuitry, and wherein assembling the battery with the circuit board includes coupling the mechanical connectors and electrical connectors of the battery housing to each other, such that by virtue of the mechanical connectors connecting the battery housing to the circuit board, the electrical connectors electrically couple the second pole of the battery to the electronic circuitry.

Inventive concept 19. The method according to Inventive concept 18, wherein the circuit board is shaped to define slots, wherein the mechanical connectors include protrusions, and wherein assembling the battery with the circuit board includes clicking the protrusions into respective slots of the circuit board.

Inventive concept 20. The method according to Inventive concept 18, wherein assembling the battery with the circuit board does not include electrically coupling the second pole of the battery to the electronic circuitry using any additional electrical coupling elements other than the electrical connectors.

There is still further provided, in accordance with an Inventive concept 21 of the present invention, apparatus for use with a power supply, the apparatus including an apparatus, which includes:

a battery including first and second poles;

a circuit board that includes electronic circuitry, the second pole of the battery being electrically coupled to the electronic circuitry; and a battery-isolation tab removably disposed between the first pole and the electronic circuitry, the battery-isolation tab including:

a non-conductive substrate configured to electrically isolate the first pole from the electronic circuitry, while the battery-isolation tab is disposed between the first pole and the electronic circuitry;

a first conductive layer disposed upon the non-conductive substrate, the first conductive layer being electrically coupled to the electronic circuitry, while the battery-isolation tab is disposed between the first pole and the electronic circuitry;

a second conductive layer disposed upon the non-conductive substrate, the second conductive layer being electrically coupled to the second pole of the battery, while the battery-isolation tab is disposed between the first pole and the electronic circuitry, wherein the first and the second conductive layers are electrically isolated from each other and are configured to facilitate electrical coupling of the power supply to the electronic circuitry, while the battery-isolation tab is disposed between the first pole and the electronic circuitry, and wherein the apparatus is configured such that the first pole of the battery is in electrical contact with the electronic circuitry of the circuit board, while the battery-isolation tab is not disposed between the first pole and the electronic circuitry.

Inventive concept 22. The apparatus according to Inventive concept 21, further including first and second leads, which are configured to electrically couple the first and the second conductive layers to respective poles of the power supply, thereby electrically coupling the power supply to the electronic circuitry.

Inventive concept 23. The apparatus according to Inventive concept 21 or Inventive concept 22, wherein the first and the second conductive layers include printed conductive layers that are printed upon the non-conductive substrate.

Inventive concept 24. The apparatus according to Inventive concept 21 or Inventive concept 22, wherein the apparatus further includes electrodes, which are configured to be adhered to skin of a subject, wherein the electronic circuitry is configured to drive the electrodes to drive a current into the subject's skin.

There is additionally provided, in accordance with an Inventive concept 25 of the present invention, a method for manufacturing an apparatus, the method including:

assembling a battery, which includes first and second poles, with a circuit board that includes electronic circuitry, such that (a) the second pole of the battery is electrically coupled to the electronic circuitry, and (b) a battery-isolation tab is removably disposed between the first pole and the electronic circuitry, such that a non-conductive substrate of the battery-isolation tab electrically isolates the first pole from the electronic circuitry;

while the battery-isolation tab is removably disposed between the first pole and the electronic circuitry, temporarily electrically coupling a power supply, separate from the battery, to the electronic circuity via (a) a first conductive layer disposed upon the non-conductive substrate, the first conductive layer being electrically coupled to the electronic circuitry, and (b) a second conductive layer disposed upon the non-conductive substrate, the second conductive layer being electrically coupled to the second pole of the battery, wherein the first and the second conductive layers are electrically isolated from each other; and while the power supply is temporarily electrically coupled to the electronic circuitry, testing functionality of the electronic circuitry, wherein the apparatus is configured such that the first pole of the battery is in electrical contact with the electronic circuitry of the circuit board upon removal of the battery-isolation tab from between the first pole and the electronic circuitry after manufacturing of the apparatus.

Inventive concept 26. The method according to Inventive concept 25, wherein electrically coupling the power supply to the electronic circuitry includes using first and second leads to electrically couple the first and the second conductive layers to respective poles of the power supply, thereby electrically coupling the power supply to the electronic circuitry.

Inventive concept 27. The method according to Inventive concept 25 or Inventive concept 26, wherein the first and the second conductive layers include printed conductive layers that are printed upon the non-conductive substrate.

Inventive concept 28. The method according to Inventive concept 25 or Inventive concept 26, wherein the apparatus further includes electrodes, which are configured to be adhered to skin of a subject, wherein the electronic circuitry is configured to drive the electrodes to drive a current into the subject's skin.

There is yet additionally provided, in accordance with an Inventive concept 29 of the present invention, apparatus including:

a set of first and second electrodes configured to be placed in electrical contact with a portion of a body of a subject; and at least one computer processor configured to drive the electrodes to apply an electrical stimulation signal into the portion of the subject's body, by:

driving a plurality of alternating current cycles into the portion of the subject's body, each of the current cycles containing a positive portion and a negative portion;

every N cycles, reversing a direction in which the current cycle is driven between the first and second electrodes, N being an integer.

Inventive concept 30. The apparatus according to Inventive concept 29, wherein N is an integer between 1 and 10.

Inventive concept 31. The apparatus according to any one of Inventive concepts 29-30, wherein the computer processor is configured to drive the electrodes to apply the electrical stimulation signal into the portion of the subject's body such that the amount of positive charge that is delivered during the positive portion of each of the cycles is approximately equal to the amount of negative charge that is delivered during the negative portion of each of the cycles.

Inventive concept 32. The apparatus according to any one of Inventive concepts 29-30, wherein the computer processor is configured to drive, into the portion of the subject's body, a plurality of pulses during the positive portion of each of at least some of the current cycles, and a plurality of pulses during the negative portion of each of at least some of the current cycles.

There is also provided, in accordance with an Inventive concept 33 of the present invention, apparatus including:

a set of first and second electrodes configured to be placed in electrical contact with a portion of a body of a subject; and at least one computer processor configured to drive the electrodes to apply an electrical stimulation signal into the portion of the subject's body, by:

driving a plurality of alternating current cycles into the portion of the subject's body, each of the current cycles containing a positive portion and a negative portion;

repeatedly reversing a direction in which the current cycle is driven between the first and second electrodes.

Inventive concept 34. The apparatus according to Inventive concept 33, wherein the at least one computer processor is configured to repeatedly reverse the direction in which the current cycle is driven in repetition periods measured in current cycles.

Inventive concept 35. The apparatus according to Inventive concept 33, wherein the at least one computer processor is configured to repeatedly reverse the direction in which the current cycle is driven in repetition periods measured in units of time.

Inventive concept 36. The apparatus according to any one of Inventive concepts 33-35, wherein the computer processor is configured to drive the electrodes to apply the electrical stimulation signal into the portion of the subject's body such that the amount of positive charge that is delivered during the positive portion of each of the cycles is approximately equal to the amount of negative charge that is delivered during the negative portion of each of the cycles.

There is further provided, in accordance with an Inventive concept 37 of the present invention, apparatus including:

a circuit board that includes electronic circuitry;

a battery including first and second poles; and a battery housing configured to house the battery, such that the second pole of the battery is in contact with at least a portion of the electronic circuitry, the battery housing including:

mechanical connectors configured to mechanically connect the battery housing to the circuit board; and electrical connectors configured to electrically couple the second pole of the battery to the electronic circuitry, the mechanical connectors and electrical connectors of the battery housing being coupled to each other, such that by virtue of the mechanical connectors connecting the battery housing to the circuit board, the electrical connectors electrically couple the second pole of the battery to the electronic circuitry.

Inventive concept 38. The apparatus according to Inventive concept 37, wherein the circuit board is shaped to define slots, and wherein the mechanical connectors include protrusions that are configured to click into respective slots of the circuit board.

Inventive concept 39. The apparatus according to Inventive concept 37 or Inventive concept 38, wherein the second pole of the battery is not electrically coupled to the electronic circuitry using any additional electrical coupling elements other than the electrical connectors.

There is still further provided, in accordance with an Inventive concept 40 of the present invention, apparatus including:
a patch including:
a circuit board that includes electronic circuitry;
skin-contacting electrodes configured to come into electrical contact with skin of a subject;
a hydrogel layer underneath the skin-contacting electrodes, the hydrogel layer being configured to adhere the patch to the subject's skin;
a set of current-outputting electrodes disposed between the circuit board and the skin-contacting electrodes; and
a set of current-receiving electrodes disposed between the circuit board and the skin-contacting electrodes,
the electronic circuitry being configured to test a connectivity of the skin-contacting electrodes, without driving any current through the hydrogel layer, by driving a test current into the skin-contacting electrodes via the current-outputting electrodes, and detecting that the outputted current is received by the current-receiving electrodes.

There is additionally provided, in accordance with an Inventive concept 41 of the present invention, a method including:
testing connectivity of skin-contacting electrodes of a patch,
the patch including:
a circuit board that includes electronic circuitry;
the skin-contacting electrodes configured to come into electrical contact with skin of a subject;
a hydrogel layer underneath the skin-contacting electrodes, the hydrogel layer being configured to adhere the patch to the subject's skin;
a set of current-outputting electrodes disposed between the circuit board and the skin-contacting electrodes; and
a set of current-receiving electrodes disposed between the circuit board and the skin-contacting electrodes,
the testing including testing the connectivity of the skin-contacting electrodes, without driving any current through the hydrogel layer, by:
driving a test current into the skin-contacting electrodes via the current-outputting electrodes; and
detecting that the outputted current is received by the current-receiving electrodes.

There is yet additionally provided, in accordance with an Inventive concept 42 of the present invention, apparatus including:
a patch including a set of first and second electrodes configured to be placed in electrical contact with skin of a subject; and
electronic circuitry configured to:
operate the patch in a standby mode;
detect that the electrodes have come into contact with the subject's skin; and
automatically switch the patch from the standby mode to an electrical-stimulation mode in response to detecting that the electrodes have come into contact with the subject's skin, the electrodes being configured to drive a current into the subject's skin, when in the electrical-stimulation mode.

Inventive concept 43. The apparatus according to Inventive concept 42, wherein the electronic circuitry is configured to detect that the electrodes have come into contact with the subject's skin by detecting a change in a parameter selected from the group consisting of: impedance between the electrodes, resistance between the electrodes, and capacitance between the electrodes.

The present invention will be more fully understood from the following detailed description of embodiments thereof, taken together with the drawings, in which:

BRIEF DESCRIPTION OF THE DRAWINGS

FIGS. 2A, 2B, and 2C are schematic illustrations of respective external views of the patch of FIG. 1, in accordance with some applications of the present invention.

DETAILED DESCRIPTION OF APPLICATIONS

Figure 1:
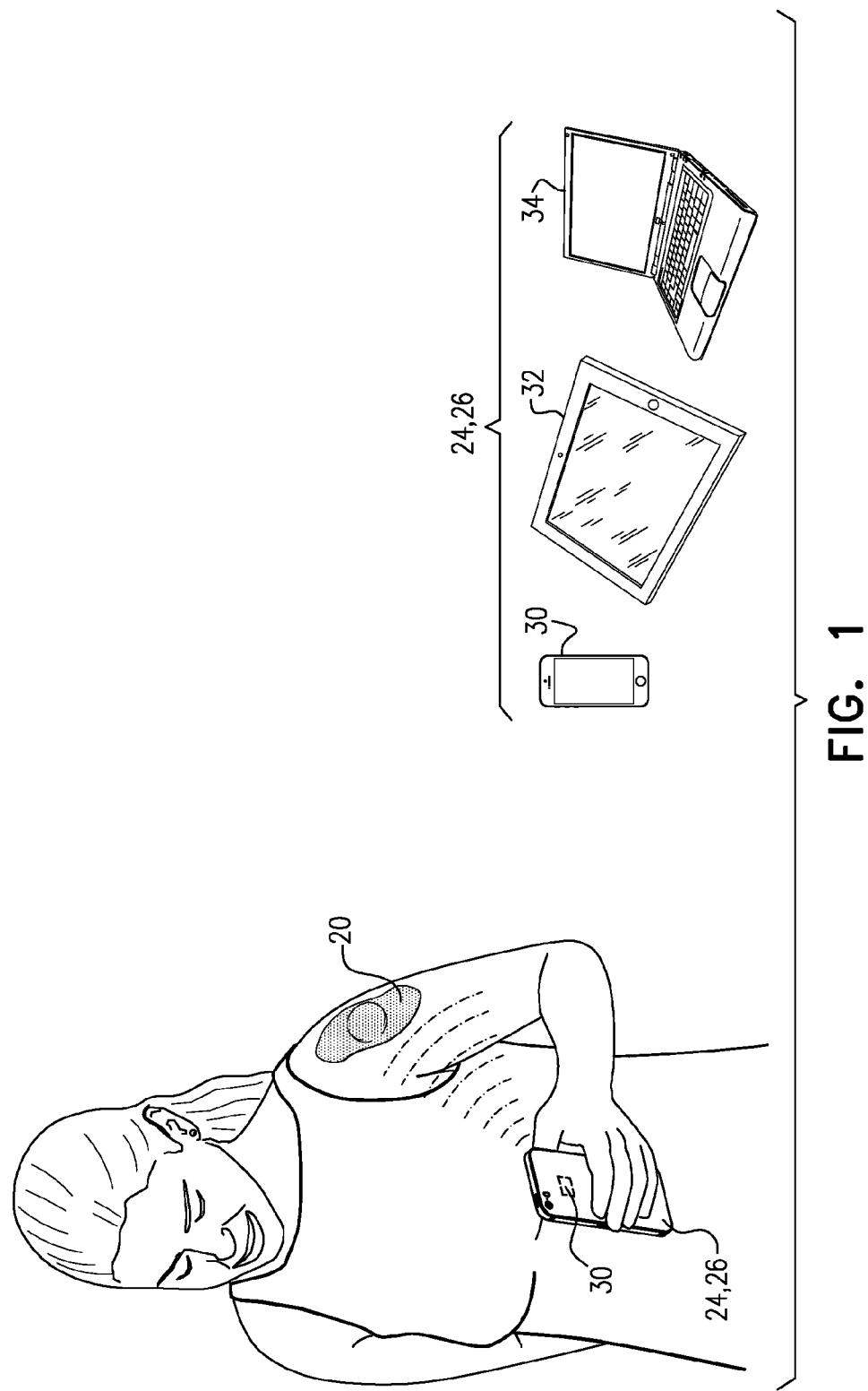
FIG. 1 is a schematic illustration of an electrode patch for applying an electrical signal to a subject, a computer processor, and a user interface, in accordance with some applications of the present invention.

Reference is now made to FIG. 1, which is a schematic illustration of an electrode patch 20 disposed on a subject's arm, a computer processor 24, and a user interface 26, in accordance with some applications of the present invention. Although patch 20, as shown in FIG. 1, is disposed on the subject's arm, the scope of the present application includes a patch that is configured to be placed on any part of a subject's body, including, but not limited to, a subject's arms, upper arms, legs, upper legs, hands, feet, abdomen, lower abdomen, ankles, torso, back, neck, head, face, etc. Patch 20 typically comprises electrodes which are configured to come into electrical contact with the subject's skin. In accordance with respective applications, the electrodes are configured to drive a current into the subject's skin, and/or to receive an electrical signal (e.g., an EMG signal) from the subject's skin.

Reference is now made to FIGS. 2A, 2B, and 2C, which are schematic illustration of respective external views of patch 20, in accordance with some applications of the present invention. As indicated, a central portion 40 of the patch is typically raised, since it contains many of the electronic components of the patch, as described in further detail hereinbelow. Typically, the thickness of the patch at the areas of the patch that surround the central portion is more than 0.5 mm, and/or less than 5 mm, e.g., between 0.5 mm and 5 mm. Further typically, the thickness of the patch at the central portion is more than 6 mm, and/or less than 15 mm, e.g., between 6 mm and 15 mm. For some applications, a length L of the patch is more than 5 cm (e.g., more than 10 cm), and/or less than 20 cm (e.g., less than 15 cm), for example, between 5 cm and 20 cm, or between 10 cm and 15 cm. For some applications, a width W of the patch is more than 3 cm (e.g., more than 5 cm), and/or less than 9 cm (e.g., less than 7 cm), for example, between 3 cm and 9 cm, or between 5 cm and 7 cm. As shown in FIGS. 2A and 2B, typically the patch is packaged with a battery-isolation tab 42 disposed within the patch, the battery-isolation tab being as described in further detail hereinbelow.

Figure 3:
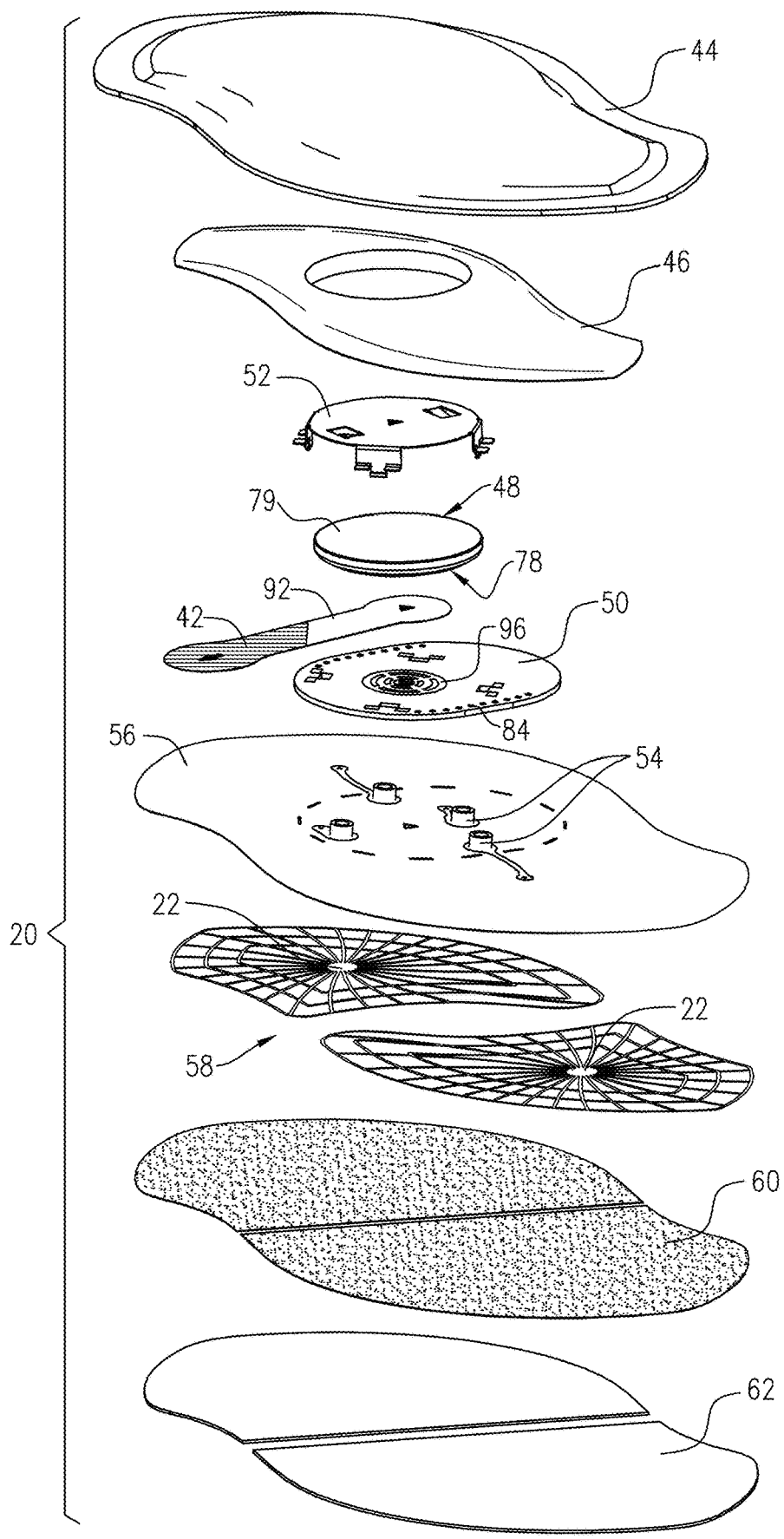
FIG. 3 is a schematic exploded view of the patch of FIG. 1, in accordance with some applications of the present invention.

Reference is now made to FIG. 3, which is a schematic exploded view of patch 20, in accordance with some applications of the present invention. As shown in FIG. 3, patch 20 is typically assembled from a plurality of layers. For some applications, the patch comprises a first upper protective layer 44 and a second protective layer 46. The first and second layers are configured to protect the inner layers of the patch, which are underneath the protective layers. As used in the present application, including in the claims, "underneath" means lower than, i.e., farther from first upper protective layer and closer to hydrogel layer 60, which is configured to adhere the patch to the subject's skin, as described hereinbelow. For some applications, the first upper protective layer is made of a polymer, such as polyvinyl chloride, and the second protective layer is a foam layer made of a polymer, such as polyethylene, and/or polyurethane. Typically, the patch comprises a battery 48 (which is typically a coin battery as shown), a circuit board 50 (e.g., a printed circuit board) that contains electronic circuitry 53 (labeled in FIG. 5B), and a battery housing 52, which is configured to house the battery as well as to provide an electrical connection between the battery and the electronic circuitry of the circuit board, as described in further detail hereinbelow. For example, battery 48 may be a coin battery as shown, or another type of primary cell battery (e.g., Lithium-thionyl chloride [Li-SOCl2], Lithium Manganese Dioxide[Li/MnO2] or the like. As described hereinabove, the patch is typically supplied to a user with battery-isolation tab 42 disposed therein. The battery-isolation tab is configured to electrically separate the battery from the electronic circuitry of the circuit board, such that the battery does not drain prior to use of the patch. As described hereinbelow, the battery-isolation tab is further configured to temporarily facilitate electrical coupling of the battery to the electronic circuitry of the circuit board, such that, for example, functionality of the electronic circuitry of the circuit board may be tested during manufacture of the patch, such as during a testing stage of manufacture of the patch. (As is known in the art, manufacturing of medical devices such the patch include testing components of the patch before, during, and/or after assembly of the components thereof, typically prior to final packaging of the patch.

Typically, the patch additionally comprises an upper printed layer 56 and a lower printed layer 58, each of the printed layers having patterns of a conductive material printed thereon, as described in further detail hereinbelow. The upper and lower printed layers are typically both disposed underneath the printed circuit board. For some applications, the upper printed layer is separated from the printed circuit board via spacing elements 54. Typically, the spacing elements are made of an electrically conductive material (e.g., a metal), and are configured to provide electrical coupling between the circuit board and the upper printed layer. In turn, the upper printed layer is typically electrically coupled to the lower printed layer. The lower printed layer defines electrodes 22, via which electrical stimulation is applied to a subject. For some applications, electrodes 22 are used for sensing an electrical signal of the subject.

Typically, a hydrogel layer 60 is disposed underneath lower printed layer 58, the hydrogel layer being configured (a) to adhere the patch to the subject's skin, and (b) to electrically couple the lower printed layer to the subject's skin. For some applications, portions of patch 20, such as electrodes 22 and the hydrogel layer, comprise an electrode manufactured by Axelgaard Manufacturing Co., Ltd. (Fallbrook, CA, USA), such as UltraStim® Snap electrodes (e.g., Part Number SN2020) or UltraStim® Garment electrodes (e.g., Part Number US2020). Typically, prior to the patch being applied to the subject's skin, the patch is supplied to the user with a liner 62 covering the hydrogel layer. The liner is typically removable. For some applications, the liner comprises a polyester film, in order to facilitate removal of the liner from the hydrogel.

Figure 4A:
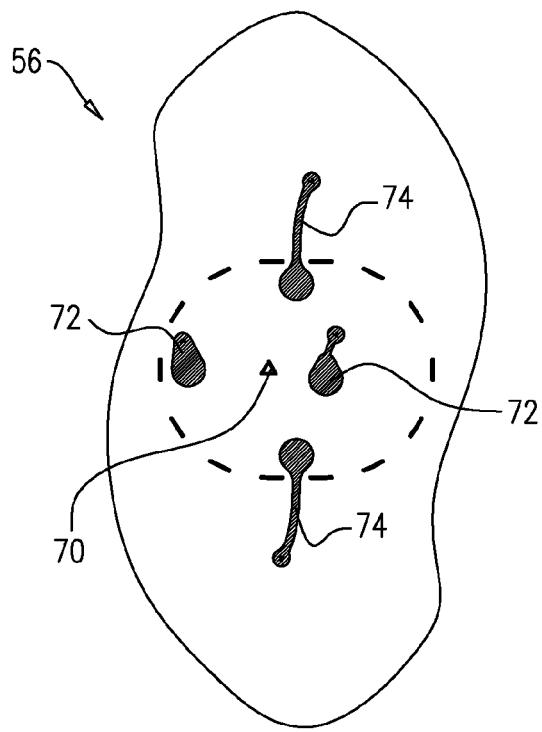
FIGS. 4A and 4B are schematic illustrations of, respectively, upper and lower printed layers of the patch of FIG. 1, the printed layers having patterns of a conductive material printed thereon, in accordance with some applications of the present invention.
Figure 4B:
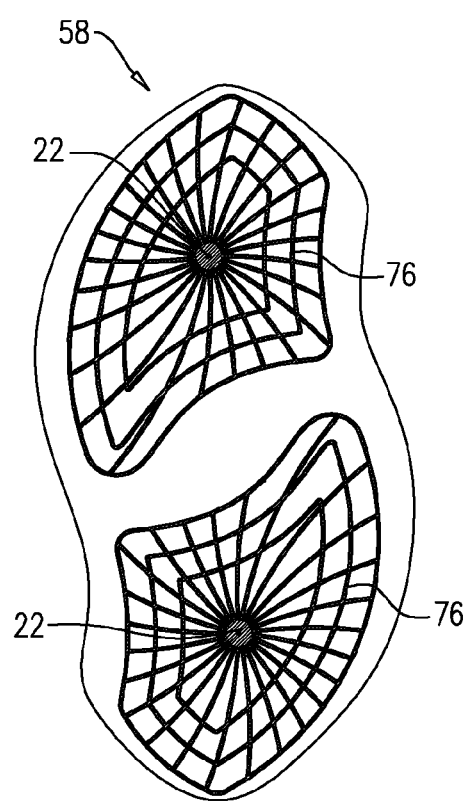

Reference is now made to FIGS. 4A and 4B, which are schematic illustrations of, respectively, upper printed layer 56 and lower printed layer 58 of patch 20, in accordance with some applications of the present invention. For some applications, the upper and lower printed layers are made of a conductive layer (which typically comprises conductive materials, such as, include silver, silver/silver chloride, carbon, graphene, nickel, iron, tungsten, bismuth, zinc, PEDOT, and/or blends such as platinized carbon) printed upon a substrate (such as polyester (PET, PEN), polycarbonate (PC), paper, polyimide (PI), and/or polyetherimide (PEI)). Typically, the patterns of conductive material are printed on both sides of each of the layers. For some applications, the conductive material of the lower layer is shaped in to a plurality of grids 76 (e.g., two grids 76, as shown), each of the grids defining a central focal point, which acts as electrode 22, for applying an electrical signal to a subject, and/or sensing an electrical signal from the subject.

For some applications, the upper printed layer comprises an alignment marker 70, which is configured to facilitate the alignment of the upper printed layer with the printed circuit board during assembly of the patch. Typically, the conductive material of the upper printed layer defines a plurality of current-outputting electrodes 72, configured for driving a current into the conductive material of the lower printed layer. For some applications, the conductive material of the upper printed layer additionally defines a plurality of current-receiving electrodes 74, which are configured to receive a current from the conductive material of the lower printed layer. For some applications, the connectivity of electrodes 22 (defined by the lower printed layer) is tested during manufacture of patch 20, such as a testing stage of manufacture of patch 20, using current-outputting electrodes 72 and current-receiving electrodes 74 of the upper printed layer of the patch. In this manner, the connectivity of electrodes 22 is tested by circuit board 50, without any current needing to be driven through hydrogel layer 60. Thus, the connectivity of electrodes 22 may be tested without having to remove liner 62, and while maintaining the hydrogel layer in an unused and sterile state. Typically, in order to test the connectivity of the electrodes, electronic circuitry 53 within the circuit board drives a test current toward electrode 22, via current-outputting electrodes 72. In response to detecting that the outputted current is received by current-receiving electrodes 74 (which are typically electrically coupled to grids 76 of the lower conductive layer), the circuitry determines that the electrodes are properly connected.

Figure 5A:
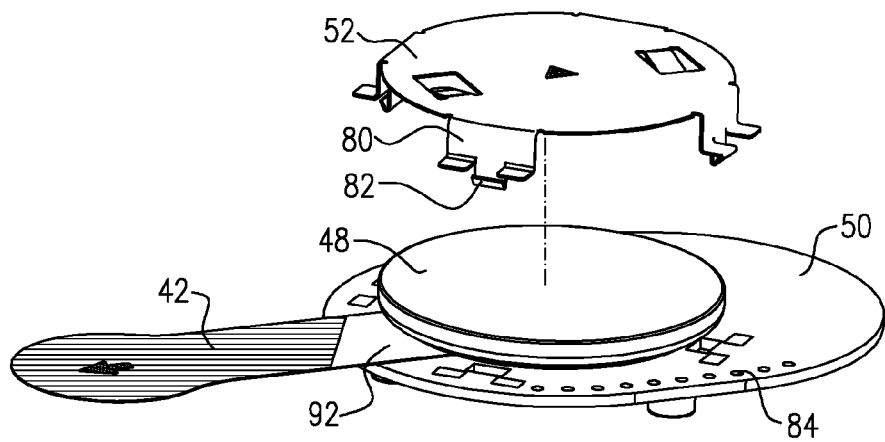
FIGS. 5A, 5B, 5C, and 5D are schematic illustrations of respective components of the patch of FIG. 1, in accordance with some applications of the present invention.

Reference is now made to FIGS. 5A, 5B, 5C, and 5D, which are schematic illustrations of respective components of patch 20 for applying an electrical signal to a subject, in accordance with some applications of the present invention. FIG. 5A shows coin battery 48, circuit board 50, and battery housing 52. Typically, the circuit board is a printed circuit board that contains electronic circuitry 53 that is configured to drive electrodes 22 to drive a current into the subject's skin, and or is configured to receive an electrical signal from the subject's skin. For some applications, the battery housing is configured to house the battery, such that a first pole 78 of the battery (e.g., the negative pole) (labeled in FIG. 3 as the bottom, underneath side of the battery) is in electrical contact (e.g., directly electrical contact) with at least a portion of the electronic circuitry of the circuit board (at least once the battery-isolation tab has been removed). (Alternatively, first pole 78 may be the positive pole of the battery.) For some applications, battery housing 52 comprises mechanical connectors 80 configured to mechanically connect the battery housing to the printed circuit board. For example, the mechanical connectors may comprise protrusions that are configured to click into slots defined by the printed circuit board.

For some applications, the battery housing additionally comprises electrical connectors 82, which are configured to electrically couple a second pole 79 of the battery (e.g., the positive pole) (labeled in FIG. 3 as the top side of the battery) to the electronic circuitry of the circuit board. (Alternatively, second pole 79 may be the negative pole of the battery.) Typically, mechanical connectors 80 and electrical connectors 82 of the battery housing are coupled to each other, such that by virtue of the mechanical connectors connecting the battery housing to the printed circuit board, the electrical connectors electrically couple second pole 79 of the battery to the electronic circuitry of the circuit board. Typically, the electrical connectors do not require any additional coupling to the electronic circuitry of the circuit board. For example, the electrical connectors are typically not required to be soldered to the printed circuit board.

Figure 5B:
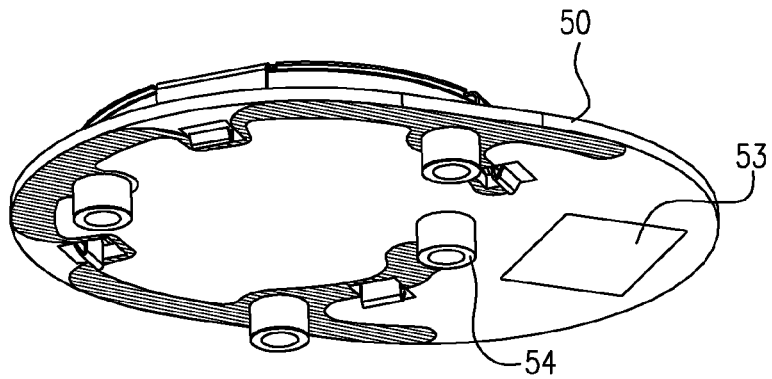

FIG. 5B shows the underside of circuit board 50, electrically conductive spacing elements 54 being coupled to the underside of the circuit board, in accordance with some applications of the present invention. Typically, electrically conductive spacing elements 54 are configured to electrically couple the circuit board to respective electrodes of the current-outputting electrodes 72 and current-receiving electrodes 74 of upper printed layer 56.

Figure 5C:
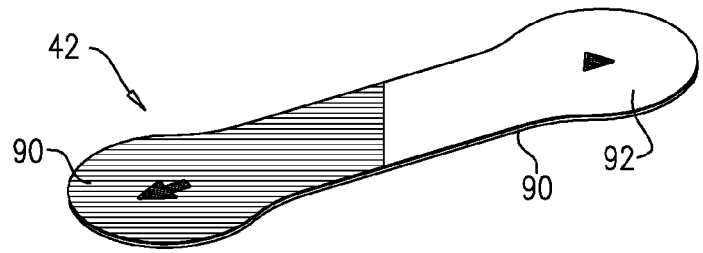

FIG. 5C shows battery-isolation tab 42, in accordance with some applications of the present invention. For some applications, the battery-isolation tab comprises a non-conductive substrate 90 (such as polyester (PET, PEN), polycarbonate (PC), paper, polyimide (PI), and/or polyetherimide (PEI)), with a conductive layer 92 (which typically comprises conductive materials, such as, silver, silver/silver chloride, carbon, graphene, nickel, iron, tungsten, bismuth, zinc, PEDOT, and/or blends such as platinized carbon) disposed (e.g., printed) upon at least a portion of one side of non-conductive substrate 90.

Typically, when the patch is manufactured (typically during assembly of the battery with the circuit board), battery-isolation tab 42 is placed between one of the poles of the battery (e.g., first pole 78, which may be the negative pole, as mentioned above), and a corresponding electrical connection 96 (labeled in FIG. 3) on the electronic circuitry of the circuit board. Typically, the battery-isolation tab is configured to electrically separate the battery from the electronic circuitry of the circuit board, such that the battery does not drain prior to use of the patch. For some applications, conductive layer 92 is configured to temporarily facilitate electrical coupling of the battery to the electronic circuitry of the circuit board, such that, for example, functionality of the electronic circuitry of the circuit board may be tested during manufacture of patch 20, such as during a testing stage of manufacture of the patch. For example, the circuit board may be tested wirelessly, e.g., using a wireless protocol such as Bluetooth®.

Figure 5D:
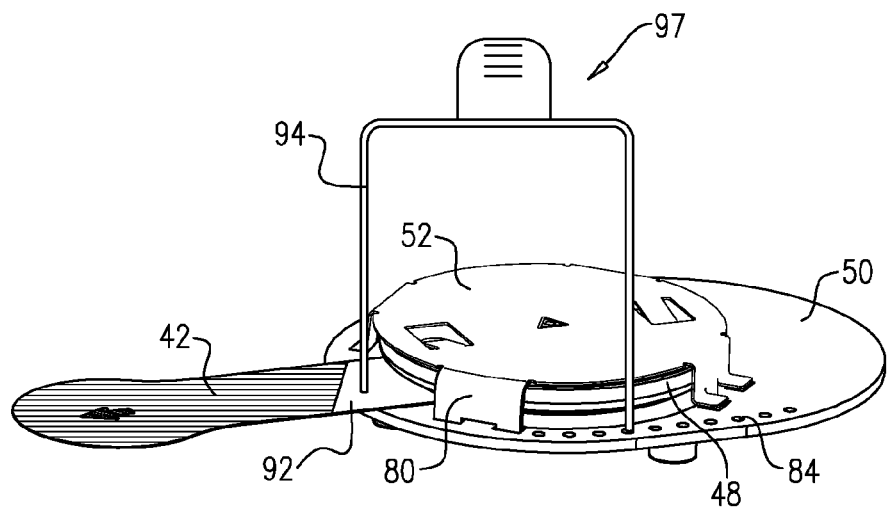

FIG. 5D shows coin battery 48, circuit board 50, and battery housing 52 upon assembly together thereof, and additionally highly schematically shows a dedicated test jig 97. Typically, in order to test the functionality of electronic circuitry 53 of circuit board 50 during manufacture of patch 20, battery-isolation tab 42 is left in place. An electrical connecting element 94 (e.g., a lead, which may optionally be an element of test jig 97 (as shown) (e.g., comprising one or more pogo pins) or a dedicated test head (not shown)) is electrically coupled to conductive layer 92 of battery-isolation tab 42, as well as to a test point 84 on the electronic circuitry of the circuit board (shown in FIG. 5A). Test point 84 is electrically coupled to electrical connection 96 (labeled in FIG. 3). In this manner, the pole of the battery (e.g., first pole 78) that was isolated from electronic circuitry 53 of circuit board 50 is temporarily electrically coupled to the electronic circuitry of the circuit board, via conductive layer 92, electrical connecting element 94, and test point 84. As described hereinabove, second pole 79 of the battery is electrically coupled to the electronic circuitry of the circuit board via battery housing 52. Thus, the electronic circuitry of the circuit board is electrically connected to the positive and negative poles of the battery, and its functionality may be tested during manufacture of patch 20. For example, the circuit board may be tested wirelessly, e.g., using a wireless protocol such as Bluetooth®.

Subsequently, electrical connecting element 94 is removed, such that the pole of the battery (e.g., first pole 78) is again isolated from electronic circuitry 53 of circuit board 50, until the patch is ready for use. At a further subsequent time, when the patch is ready to be used by a patient, battery-isolation tab 42 is permanently removed, such that the pole of the battery (e.g., first pole 78) is directly connected to the electronic circuitry of the circuit board.

Figure 5E:
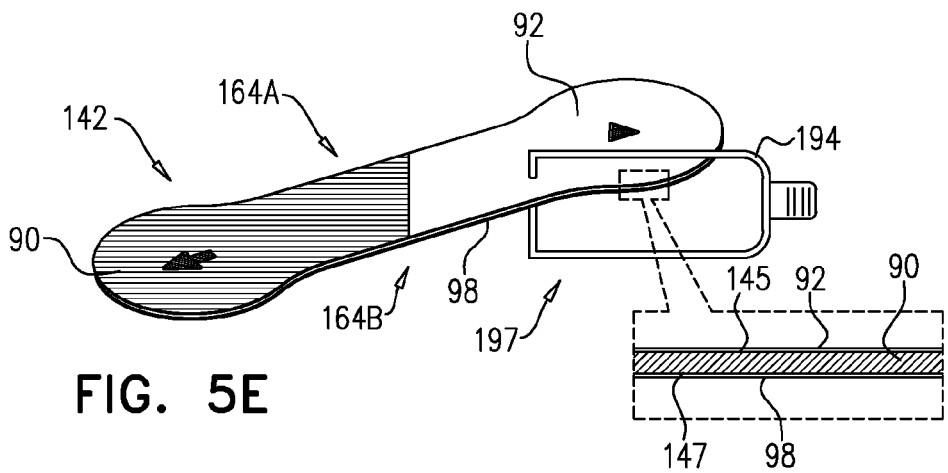
FIGS. 5E and 5F are schematic illustrations of another battery-isolation tab, in accordance with an application of the present invention.
Figure 5F:
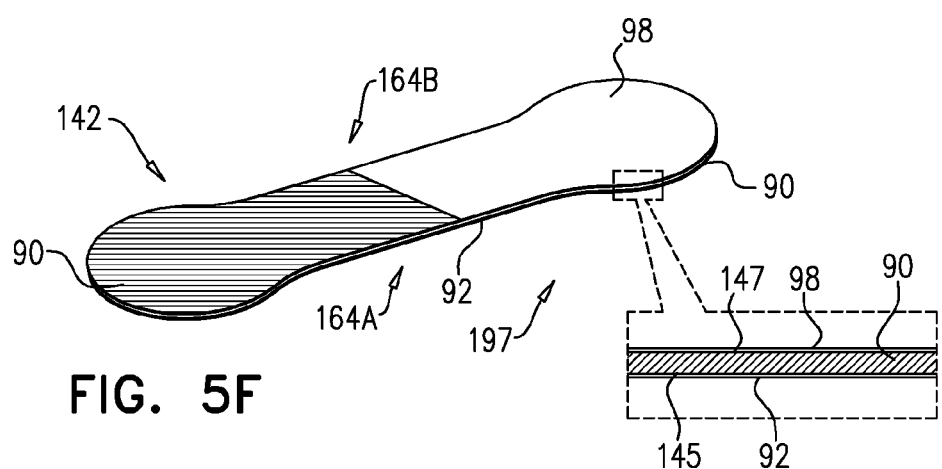

Reference is made to FIGS. 5E and 5F, which are schematic illustrations of a battery-isolation tab 142, in accordance with an application of the present invention. FIG. 5E shows a top side 164A of the tab, and FIG. 5F shows a bottom (underneath) side 164B of the tab. FIG. 5E additionally highly schematically shows a dedicated test jig 197. Other than as described below, battery-isolation tab 142 is identical to battery-isolation tab 42, described hereinabove with reference to FIGS. 2A-5D, and may implement any of the features of battery-isolation tab 42 and may be used as described above. It is noted that testing using the techniques described with reference to FIGS. 5E and 5F may optionally be performed even after complete assembly of patch 20, as shown in FIGS. 2A-C.

In addition to comprising non-conductive substrate 90 and conductive layer 92 as an upper conductive layer on at least a portion of a top surface 145 of non-conductive substrate 90, described hereinabove with reference to FIG. 5C, battery-isolation tab 142 further comprises a lower conductive layer 98 on at least a portion of a bottom (underneath) surface 147 of non-conductive substrate 90. (Typically, first pole 78 is in electrical contact with upper conductive layer while the battery-isolation tab is disposed between the first pole and electronic circuitry 53.) Non-conductive substrate 90 electrically isolates upper conductive layer 92 and lower conductive layer 98 from each other, such that when battery-isolation tab 142 is disposed (typically during manufacture of the patch) between one of the poles of the battery (e.g., first pole 78) and corresponding electrical connection 96, battery-isolation tab 142 is configured to electrically separate the battery from electronic circuitry 53 of circuit board 50, such that the battery does not drain prior to use of the patch, such as described hereinabove regarding battery-isolation tab 42.

Typically, in order to test the functionality of electronic circuitry 53 of circuit board 50 during manufacture of patch 20, battery-isolation tab 142 is left in place. An electrical connecting element 194 (e.g., a lead, which may optionally be an element of test jig 197 (as shown) or a dedicated test head (not shown)) is electrically coupled to both upper conductive layer 92 and lower conductive layer 98 of battery-isolation tab 142. In this manner, the pole of the battery (e.g., first pole 78) that was isolated from the electronic circuitry of the circuit board is temporarily electrically coupled to the electronic circuitry of the circuit board, via upper conductive layer 92, electrical connecting element 194, lower conductive layer 92, and electrical connection 96. As described hereinabove, second pole 79 of the battery is electrically coupled to the electronic circuitry of the circuit board via battery housing 52. Thus, the electronic circuitry of the circuit board is electrically connected to the positive and negative poles of the battery, and its functionality may be tested during manufacture of patch 20. For example, the circuit board may be tested wirelessly, e.g., using a wireless protocol such as Bluetooth®.

Subsequently, electrical connecting element 194 is removed, such that the pole of the battery (e.g., first pole 78) is again isolated from electronic circuitry 53 of circuit board 50, until the patch is ready for use. At a further subsequent time, when the patch is ready to be used by a patient, battery-isolation tab 142 is permanently removed, such that the pole of the battery (e.g., first pole 78) is directly connected to the electronic circuitry of the circuit board.

Figure 5G:
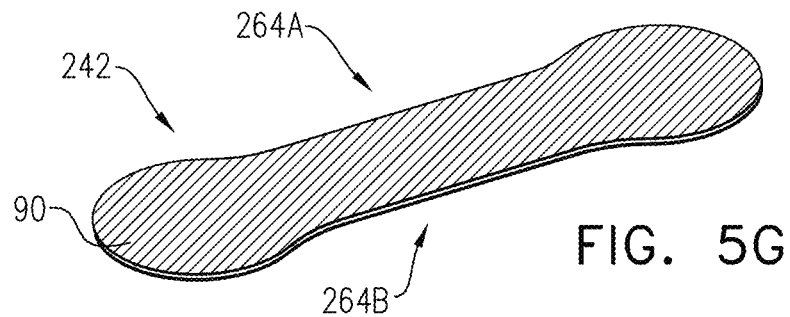
FIGS. 5G and 5H are schematic illustrations of a yet another battery-isolation tab, in accordance with an application of the present invention.
Figure 5H:
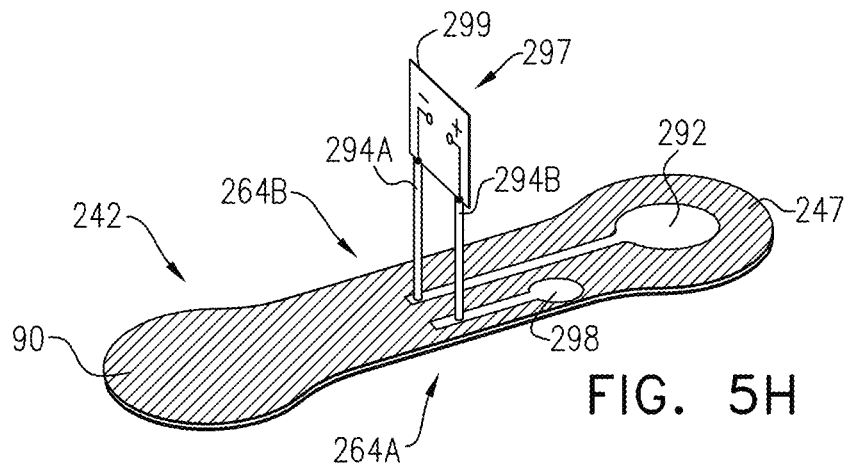

Reference is made to FIGS. 5G and 5H, which are schematic illustrations of a battery-isolation tab 242, in accordance with an application of the present invention. FIG. 5G shows a top side 264A of the tab, and FIG. 5H shows a bottom (underneath) side 264B of the tab.

Figure 5I:
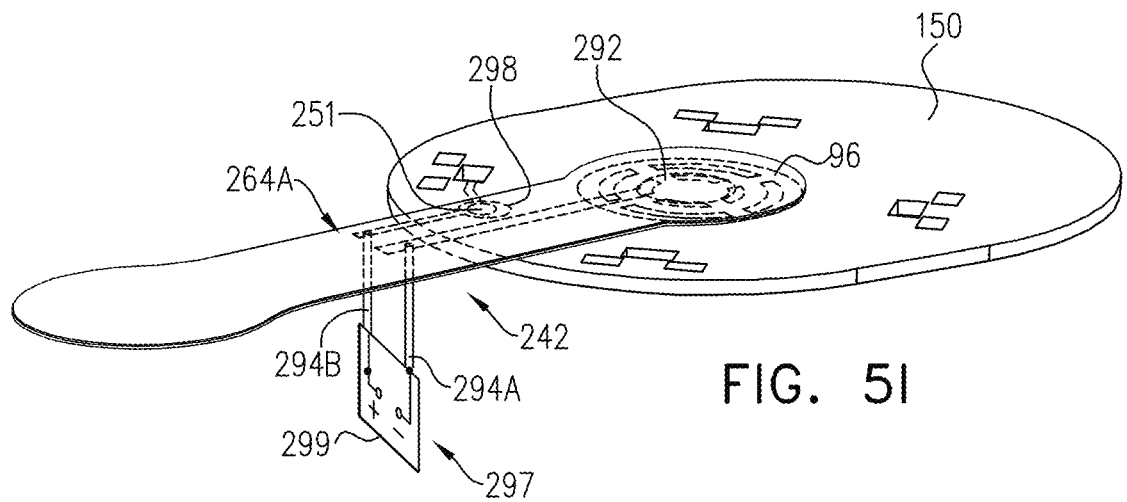
FIG. 5I is a schematic illustration of a circuit board and the battery-isolation tab of FIGS. 5G and 5H, in accordance with an application of the present invention.

Reference is additionally made to FIG. 5I, which is a schematic illustration of a circuit board 150 and battery-isolation tab 142, in accordance with an application of the present invention. Other than as described below, circuit board 150 is identical to circuit board 50, described hereinabove with reference to FIG. 3.

FIGS. 5H and 5I additionally highly schematically show a dedicated test jig 297 that comprises a power supply 299 (separate from battery 48) and first and second leads 294A and 294B. Power supply 299 is configured to provide the same type of power as battery 48, e.g., a DC power at the same voltage and amperage as the battery. Other than as described below, battery-isolation tab 242 is identical to battery-isolation tab 42, described hereinabove with reference to FIGS. 2A-5D, and may implement any of the features of battery-isolation tab 42 and may be used as described above. It is noted that testing using the techniques described with reference to FIGS. 5G and 5H may optionally be performed even after complete assembly of patch 20, as shown in FIGS. 2A-C. (It is noted that in practice test jig 297 would not be used on battery-isolation tab 42 while the tab is not connected to other elements of the patch; the test jig is nevertheless shown in FIG. 5H for clarity of illustration of the interface between the test jig and the tab.)

Battery-isolation tab 242 comprises non-conductive substrate 90, a first conductive layer 292 on a first portion of a bottom surface 247 of non-conductive substrate 90, and a second conductive layer 298 on a second portion of bottom surface 247 of non-conductive substrate 90. First and second conductive layers 292 and 298 are electrically isolated from each other.

When battery-isolation tab 242 is disposed (typically during manufacture of the patch) between one of the poles of the battery (e.g., first pole 78) and corresponding electrical connection 96:
  non-conductive substrate 90 of battery-isolation tab 242 is configured to electrically separate the battery from electronic circuitry 53 of circuit board 150, such that the battery does not drain prior to use of the patch, such as described hereinabove regarding battery-isolation tab 42,
  first conductive layer 292 is electrically coupled with electronic circuitry 53, such as via electrical connection 96 of circuit board 150, and
  second conductive layer 298 is in electrical contact with second pole 79 of the battery, such as via a second electrical connection 251 of circuit board 150, the second electrical connection 251 electrically coupled to second pole 79 of the battery, such as via electrical connectors 82, described hereinabove with reference to FIGS. 5A-B.

Typically, in order to test the functionality of electronic circuitry 53 of circuit board 150 during manufacture of patch 20, battery-isolation tab 242 is left in place. First and second leads 294A and 294B of test jig 297 are electrically coupled to first and second conductive layers 292 and 294, respectively. Thus, electronic circuitry 53 of circuit board 150 is electrically connected to the positive and negative poles of power supply 299 of test jig 297. (First lead 294A is coupled to first conductive layer 292, which in turn is coupled with electronic circuitry 53, such as via electrical connection 96 of circuit board 150. Second lead 294B is coupled to second conductive layer 294, which in turn is coupled with second pole 79 of the battery, such as via a second electrical connection 251 of circuit board 150; as mentioned above with reference to FIGS. 5A-D, second pole 79 of the battery is coupled to electronic circuitry 53, such as via electrical connectors 82. It is noted that even though power supply 299 is electrically connected to second pole 79 of the battery, since first pole 78 of the battery is disconnected from electronic circuitry 53 and from the respective power supply pole connected to 294A by non-conductive tab layer 90 (only the second pole 79 of the battery is connected to electronic circuitry 53), current will not flow through or from the battery.) The functionality of electronic circuity 53 may thus be tested during manufacture of patch 20. For example, the circuit board may be tested wirelessly, e.g., using a wireless protocol such as Bluetooth®. In this configuration, battery 48 remains electrically isolated from electronic circuitry 53 of circuit board 150 throughout the testing procedure.

Subsequently, electrical connecting elements 294A and 294B are removed. The pole of the battery (e.g., first pole 78) remains isolated from the electronic circuitry of the circuit board, until the patch is ready for use. At a further subsequent time, when the patch is ready to be used by a patient, battery-isolation tab 242 is permanently removed, such that the pole of the battery (e.g., first pole 78) is directly connected to the electronic circuitry of the circuit board.

Reference is made to FIGS. 5A-I. For some applications, even after battery-isolation tab 42 is removed, the electronic circuitry of the circuit board is configured to operate the patch in a standby mode, in which power consumption by the patch is relatively low. For some applications, the control circuitry is configured to automatically switch the patch from the standby mode to an electrical-stimulation mode in response to detecting that electrodes 22 have come into contact with the subject's skin. Typically, in the electrical-stimulation mode, the patch is configured to communicate with user interface 26, and to apply electrical stimulation to the subject, e.g., in accordance with techniques described herein and/or in the patent applications and/or publications incorporated by reference hereinbelow. Therefore, the power consumption by the patch is typically greater when the patch is in the electrical-stimulation mode than when the patch is in standby mode. For example, the control circuitry may be configured to automatically switch the patch from the standby mode to an electrical stimulation mode in response to detecting that impedance, and/or resistance, and/or capacitance between electrodes 22 has changed.

Although the techniques described with reference to FIGS. 5A-I have been described with respect to patch 20, these techniques may also be used with other electronic devices that do not necessarily comprises electrodes 22 or other elements of patch 20.

Figure 6:
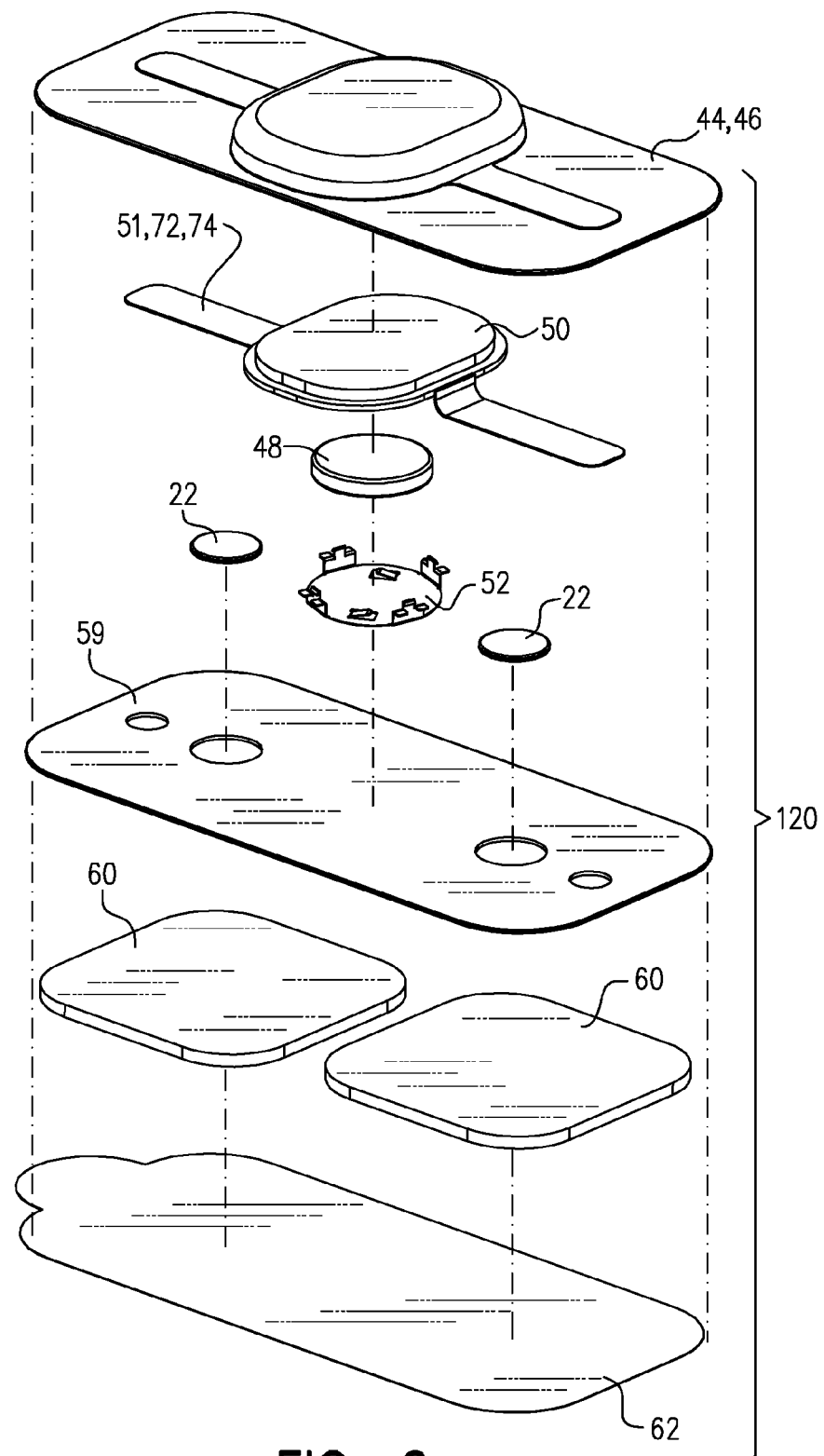
FIG. 6 is a schematic illustration of another patch for applying an electrical signal to a subject, in accordance with some alternative applications of the present invention

Reference is now made FIG. 6, which is a schematic illustration of a patch 120, in accordance with some applications of the present invention. Patch 120 as shown in FIG. 6 is generally similar to patch 20 described hereinabove with reference to FIGS. 1-5D, except for differences described hereinbelow. For some applications, the patch defines a generally rectangular shape, as shown. Typically, the dimensions of the patch are generally similar to those described hereinabove, mutatis mutandis. For some applications, patch 120 comprises a single protective layer, which combines the functionalities of layers 44 and 46 described hereinabove. Beneath the protective layer, patch 120 comprises a circuit board, e.g., printed circuit board 50 that contains electronic circuitry. For some applications, a film 51, e.g., a kapton film, is coupled to the circuit board and is configured to electrically couple electrodes 22 to the electronic circuitry of the circuit board. For example, current-outputting electrodes 72 and current-receiving electrodes 74 may be disposed on the kapton film. Coin battery 48 is typically housed within battery housing 52. Typically, the battery housing is generally similar to housing 52 as described hereinabove with reference to FIGS. 2A-5D. For some applications (not shown in FIG. 6), patch 120 comprises a battery-isolation tab, e.g., battery-isolation tab 42, 142, or 144, as described hereinabove regarding patch 20 with reference to FIGS. 3-5D, 5E-F, and 5G-I, respectively. Beneath the electrodes, the patch typically comprises hydrogel layer 60, and removable liner 62. For some applications, patch 120 additionally comprises an insulating layer 59 between the printed circuit board and the hydrogel layer.

Referring again to FIG. 1, for some applications, patch 20 as described herein is used to treat a migraine, a headache, fibromyalgia, dysmenorrhea, post-traumatic headache, premenstrual syndrome, menstrual cramps, and/or another form of pain, for example, generally in accordance with techniques described in US Patent Application Publication 2017/0368344 to Ironi et al. and/or International Patent Application No. PCT/IL2017/051087 (which published as PCT Publication WO 2018/060997 to Ironi et al.), both of which applications are incorporated herein by reference.

Typically, in response to the subject experiencing pain (such as, a migraine, a headache, fibromyalgia, dysmenorrhea, post-traumatic headache, premenstrual syndrome, menstrual cramps, and/or another form of pain) in a first anatomical region, the patch is placed on a second anatomical region of the subject body (which is a different from the first anatomical region). Typically, electrical energy is applied to the second anatomical region by driving electrical pulses into the second anatomical region, via electrodes 22 of patch 20. For some applications, the electrodes are placed at location that is at a distance of more than 25 cm from the location at which the subject is experiencing pain, and the electrical energy is applied to the location at which the electrodes are placed. Typically, by applying electrical energy at the second anatomical region, pain at the first anatomical region is reduced via the conditioned pain modulation mechanism.

Although some applications of the present invention are described as being performed using electrodes 22 disposed on patch 20, the scope of the present application includes applying electrical stimulation signals to a subject having signal characteristics as described herein, but via a different type of electrodes to those described hereinabove. For example, the stimulation may be applied via implanted electrodes, subcutaneous electrodes, and/or any other type of electrodes configured to electrically stimulate a subject.

For some applications, transcutaneous electrical energy is applied caudally to the neck of the subject using electrodes disposed on patch 20. For some applications, upon experiencing a migraine, a headache, fibromyalgia, dysmenorrhea, post-traumatic headache, premenstrual syndrome, menstrual cramps, and/or other pain, the subject places patch 20 upon a part of the subject's body, such as the subject's upper arm, as shown in FIG. 1. For some applications, the electrodes are placed on a different portion of the subject's body, such as a different location on the subject's arm, on the subject's hands, legs, feet, and/or lower abdomen (e.g., in order to treat the subject for menstrual pain, such as dysmenorrhea, premenstrual syndrome, and/or menstrual cramps). Typically, the electrodes are placed in electrical contact with the subject's skin. Further typically, electronic circuitry of the circuit board 50 controls the electrodes, in response to control signals, which are typically wirelessly received from the computer processor.

For some applications, electrical stimulation pulses are applied to a subject's skin, in order to treat a migraine, a headache, fibromyalgia, dysmenorrhea, post-traumatic headache, premenstrual syndrome, menstrual cramps, and/or another form of pain, for example, generally in accordance with techniques described in US Patent Application Publication 2017/0368344 et al. to Ironi and/or International Patent Application No. PCT/IL2017/051087 (which published as PCT Publication WO 2018/060997 to Ironi et al.). For some applications, computer processor 24 drives the electrodes to apply electrical stimulation pulses to the subject's body, such that substantially for the duration of the application of the neurostimulation (e.g., more than 90 percent of the time that that the neurostimulation is being applied) the signal that is being applied contains both a high frequency component and a low frequency component. Typically, the signal that is applied is an amplitude shift keying signal, with the high frequency component acting as a carrier wave, and the low frequency component acting as a modulating wave that modulates the carrier wave.

For some applications, the high frequency component has a frequency of more than 80 Hz (e.g., more than 90 Hz), and/or less than 120 Hz (e.g., less than 110 Hz), e.g., between 80 Hz and 120 Hz, or between 90 Hz and 110 Hz. For some applications, the low frequency component has a frequency of more than 1 Hz (e.g., more than 1.5 Hz), and/or less than 8 Hz (e.g., less than 4 Hz), e.g., between 1 Hz and 8 Hz, or between 1.5 Hz and 4 Hz. Both the high and low frequency components of the electrical simulation typically stimulate descending analgesic mechanisms. For some applications, the low frequency component primarily stimulates endorphin release, while the high frequency component primarily stimulates serotonin and/or noradrenaline release.

Typically, the high frequency component acts as a carrier wave, and the low frequency component acts as a modulating wave that modulates the carrier wave. The modulation factor is the factor by which the low frequency wave modulates the high frequency wave, during the inactive phase of the duty cycle of the low frequency signal. In other words, when the pulse of the low frequency signal is active, the overall current of the amplitude shift keying signal alternates between the nominal maximum and the nominal minimum of the amplitude shift keying signal. When the pulse of the low frequency signal is inactive, the current of the amplitude shift keying signal alternates between nominal maximum minus the modulation factor and the nominal minimum plus the modulation factor. If the modulation factor is small (i.e., close to 0), the impact of the modulating wave will be low, and (vice versa) if the modulating factor is large (i.e., close to 1), the impact of the modulating wave will be high. Typically, the modulating factor is more than 0.3 (e.g., more than 0.4), and/or less than 0.8 (e.g., less than 0.7), e.g., between 0.3 and 0.8, or between 0.4 and 0.7.

For some applications, the high frequency component of the signal drifts between 10 percent to 20 percent below its base frequency and 10 percent to 20 percent above its base frequency. For example, starting at its base frequency, the frequency of the high frequency component of the signal may be increased by 2 Hz every minute, until it reaches 10 percent to 20 percent above its base frequency. The frequency of the high frequency component of the signal may then be decreased by 2 Hz every minute, until it reaches 10 percent to 20 percent below its base frequency. Alternatively or additionally, the frequency may be increased or decreased by approximately 10 Hz every 4 to 5 minutes. For some applications, by causing the high frequency component frequency to drift, conditioning or habituation of the subject to the stimulation is reduced. That is to say that the effect of the phenomenon whereby the perceived reception of the brain to a constant stimulus declines over time is reduced.

Typically, the electrical stimulation pulses that are applied at the second anatomical region are configured such as to stimulate A-beta nerve fibers to a greater extent than any of the A-delta fibers, the C fibers, or motor nerve fibers. Further typically, more than 50 percent (e.g., more than 80 percent) of the applied electrical energy stimulates the A-beta fibers, and less than 20 percent (e.g., less than 10 percent, or less than 5 percent) of the applied energy stimulates any one of the A-delta fibers, the C fibers, and the motor nerve fibers. That is to say that each one of the A-delta, C, and motor categories of nerve fibers is stimulated by less than 20 percent (e.g., less than 10 percent, or less than 5 percent) of the applied energy. Typically, by stimulating the A-beta fibers (which are non-nociceptive) to a greater extent than the A-delta fibers, or the C fibers, the electrical pulses activate the conditioned pain modulation mechanism to thereby reduce pain at the first anatomical region, but do not cause substantial local pain (or in some cases any local pain) at the second anatomical region. Despite being non-nociceptive, stimulation of the A-beta fibers is effective at activating the conditioned pain modulation mechanism. By limiting stimulation of the A-delta and C fibers, local pain that would be caused by the stimulation of the A-delta and/or C fibers is limited. Furthermore, the stimulation of the A-beta fibers inhibits the firing of the local A-delta fibers and the C fibers, such that any local pain that might have been caused by virtue of the A-delta fibers and the C fibers having been stimulated is inhibited. By limiting stimulation of the motor fibers, any involuntary movement of the subject's muscles that may be caused by electrical stimulation of these fibers is limited, thereby reducing discomfort to the subject.

Typically, the electrical pulses that are applied at the second anatomical region are configured such as to stimulate the A-beta fibers to a greater extent than any of the A-delta fibers, the C fibers, or the motor nerve fibers, by configuring the current intensity and duration of the electrical pulses, such that both the pulse width and the current intensity of the pulses are set above the threshold levels of the A-beta nerve fibers, but below the threshold levels of A-delta fibers, C fibers, and the motor fibers.

For some applications, the pulse width is set to more than 80 microseconds (e.g., more than 120 microseconds), and/or less than 300 microseconds (e.g., less than 200 microseconds), e.g., 80-300 microseconds, or 120-200 microseconds. For some applications, the current intensity is set to more than 20 mA (e.g., more than 40 mA), and/or less than 80 mA (e.g., less than 70 mA), e.g., 20-80 mA, or 40-70 mA. It is noted that using the above-described parameters for the electrical pulses, there may still be some stimulation of the A-delta fibers, the C fibers, and/or the motor nerve fibers. However, as described hereinabove, typically, more than 50 percent (e.g., more than 80 percent) of the applied electrical energy stimulates the A-beta fibers, and less than 20 percent (e.g., less than 10 percent, or less than 5 percent) of the applied energy stimulates any one of the A-delta fibers, the C fibers, and the motor nerve fibers.

For some applications, suitable stimulation parameters for a given user are determined interactively by the user, or a caregiver of the user. For example, the user or the caregiver may gradually increase the stimulation intensity (via the user interface) until it is evident that the intensity has reached the motor threshold (e.g., by seeing or feeling muscles activity). The user or the caregiver may then slightly reduce the stimulation intensity. Typically, the current intensity threshold for motor nerve stimulation is above the A-beta threshold, but below the A-delta and C thresholds. Therefore, by slightly reducing the current intensity below the motor nerve stimulation threshold, the A-beta nerves will still be stimulated but the motor nerves, the A-delta nerves, and the C nerves will substantially not be stimulated.

For some applications, user interface 26 comprises user interface components of one or more devices, such as a smartphone 30, a tablet device 32, and/or a personal computer 34. Typically, for such applications, computer processor 24 is the computer processor of the device. It is noted that, although FIG. 1 shows the user using a smartphone as the user interface and the computer processor, the scope of the present application includes using other devices for this purpose, e.g., tablet device 32, or personal computer 34. For some applications, electronic circuitry of the circuit board 50 performs some of the computer processor functionalities that are described herein. Alternatively or additionally, the electronic circuitry of the circuit board is used to facilitate communication between a computer processor of an external device (such as smartphone 30, tablet device 32, and/or personal computer 34) and the electrodes, typically using known protocols, such as Wifi, Bluetooth®, ZigBee®, or any near field communication (NFC) protocol.

The circuit board typically comprises a central processing unit (CPU), typically programmed in microcode, that controls the electrodes, one or more memory units for storing the stimulation sequences during the stimulation, an impulse generator, and components for wireless communication. For some applications, the circuit board is an integrated system-on-chip (SoC). The circuit board typically comprises electronic circuitry, which, by way of example, may comprise components such as diodes, resistors, and capacitors, etc.

For some applications, the computer processor receives an input from the subject that indicates that the subject is experiencing a headache, a migraine, fibromyalgia, dysmenorrhea, post-traumatic headache, premenstrual syndrome, menstrual cramps, and/or other pain, via a program or application that is run on the computer processor (e.g., a program or application that is run on smartphone 30, tablet device 32, and/or personal computer 34). In response to the input, the computer processor communicates a control signal to the electronic circuitry of the circuit board. Typically, in response to receiving the control signal, the electronic circuitry of the circuit board drives the electrodes to drive electrical stimulation pulses into the subject (e.g., into the subject's upper arm, as shown in FIG. 1). For some applications, the computer processor receives an input from the subject indicating a particular treatment program, and/or control stimulation parameters (such as the intensity of the stimulation) that should be provided.

For some applications, the computer processor is configured to drive the electrodes to provide stimulation to the subject to prevent the onset of headaches, migraines, fibromyalgia, dysmenorrhea, post-traumatic headache, premenstrual syndrome, menstrual cramps, and/or other pain, before such events are sensed by the subject. For example, a stimulation treatment as described herein may be delivered at regular intervals, e.g., daily. In accordance with respective applications, the computer processor (via a program or application running on the processor) may facilitate the scheduling of such treatments, and/or may automatically alert the subject when necessary, in order to facilitate compliance with the treatment schedule.

For some applications, electrodes 22 are arranged on the patch 20 such that the current density per unit area of the skin is below 3.75 mA/cm^2. In this manner, the electrical energy that is applied via the patch generates a touch sensation to the user, but does not generate a substantial amount of local pain at the location at which the patch is placed on the subject's skin.

As described in International Patent Application No. PCT/IL2017/051087 (which published as PCT Publication WO 2018/060997 to Ironi et al.), during a period of the treatment, which may range, for example, from 20 minutes to one hour, the subject may change his/her position. Furthermore, the subject may wish to move the portion of the body (e.g., the limb) upon which electrodes 22 are placed. For example, for the application shown in FIG. 1, the subject may wish to move her arm during the treatment period. However, a stimulation dose that is applied for the pain relief therapy might be sufficiently high as to interfere with the endogenous neural stimulation sent from the brain to the motor nerves at the upper arm, or motor nerves passing through the upper arm towards the hand. Such interference might cause either difficulties in performing the required movement, and/or a sensation of discomfort.

In general, in order to reduce discomfort to the subject, the electrical stimulation dose should also be below the motor activation threshold, which differs from patient to patient, and may vary for a specific patient, depending on multiple internal and environmental factors.

Therefore, for some applications, electrodes 22 comprise stimulating electrodes that are configured to electrically stimulate the patient, by driving a current into his/her skin, as well as sensing electrodes that are configured to sense electrical parameters of the subject. The sensing electrodes are typically surface EMG electrodes and are configured to sense the EMG signal generated by motor nerves that enervate a muscle located in the vicinity of the stimulating electrodes. For some applications, the sensing electrodes are configured to sense the EMG signal generated by motor nerves that traverse a location in the vicinity of the stimulating electrodes, but that enervate a muscle located elsewhere (e.g., motor nerves passing through the upper arm towards the hand).

Typically, in response to the signal sensed by the sensing electrodes, the computer processor (or electronic circuitry of the circuit board) determines changes in the energy of the EMG of the above-described motor nerves. For example, in response to the subject starting, or attempting to move a limb upon which the electrodes are placed, the computer processor (or electronic circuitry of the circuit board) detects an increase in the EMG energy. In response thereto, the computer processor (or electronic circuitry of the circuit board) reduces the stimulation dose of the electrical stimulation that is delivered via the stimulating electrodes. (This is because the increase in the EMG energy indicates that the subject is moving or attempting to move his/her limb, and that the electrical stimulation signal may interfere with the movement or attempted movement.) Subsequently, in response to detecting that EMG energy has decreased to a given level for a given time period, the computer processor (or electronic circuitry of the circuit board) automatically increases the stimulation dose of the electrical stimulation. (This is because the decrease in the EMG energy indicates that the subject has stopped moving or attempting to move his/her limb.)

If the following denotation symbols are used:
$E_{EMG}$=momentary energy of the EMG as measured and calculated by the computer processor;
$E_{TH}$=a threshold level of EMG energy which the computer processor is configured to interpret as being indicative of limb movement or attempted movement (i.e., a movement threshold level);

$E_{HYS}$=a difference of EMG energy which the computer processor is configured to interpret as hysteresis when the limb is changing from motion to no motion status;

$D_{BASE}$=normal stimulation dose, when there is no limb motion, and therefore no need to reduce the dose;

$D_{MOTION}$=a reduced stimulation dose, to which to system adjusts in case of limb motion detection;

for some applications, the computer processor applies the following algorithm:

If $E_{EMG} < E_{TH}$, $D=D_{BASE}$ (I.e., normal operation, when there is no motion)

If $E_{EMG} > E_{TH}$, $D=D_{MOTION}$, (I.e., in case of motion detection, the stimulation dose is reduced.)

Subsequent to the dose having been reduced, if $E_{EMG} < (E_{TH} - E_{HYS})$, $D=D_{BASE}$ (I.e., subsequent to motion, the stimulation dose is re-increased only if the EMG signal drops below the movement threshold level minus an amount of energy that varies with time according to a hysteresis curve.)

For some applications, the values of $E_{TH}$ and $E_{HYS}$ are determined in an individual way for each subject. For example, initially, the subject may calibrate the computer processor, during a calibration phase, using the following technique: The stimulation dose is manually adjusted until the subject is able to feel the stimulation, but the stimulation is not painful. The subject then deliberately performs a few movements with the limb, to let the computer processor record the EMG energy changes that the subject undergoes during changes from still to motion, and from motion to still.

As described hereinabove, for some applications, after the end of motion, the stimulation dose is re-increased only if the EMG signal drops below the movement threshold value minus an amount of energy that varies with time according to a hysteresis curve. The reason for subtracting the value that varies according to a hysteresis curve is to prevent the computer processor from jumping between the normal and reduced stimulation doses, as the detected EMG passes above and below the movement threshold level. This is because the computer processor jumping between the normal and reduced stimulation doses might result in unpleasant sensation for the subject.

For some applications, the value of $D_{BASE}$ is determined based upon the stimulation parameters that the subject selects during the calibration phase, as described hereinabove. The value of $D_{MOTION}$ is typically a given percentage of $D_{BASE}$, e.g., between 50 and 90 percent, or between 60 and 80 percent, of $D_{BASE}$.

For some applications, $D_{BASE}$ is initially set as $(D_{MOTOR} - \varepsilon)$, where $D_{MOTOR}$ is the threshold for motor nerve activation, and c is a margin used to ensure that motor activation is avoided. Typically, dose adjustment (e.g., reduction of the electrical stimulation dose during limb motion) is performed by means of intensity adjustment. For some applications, pulse width and/or pulse frequency are adjusted. For some applications, the computer processor determines which of the parameters to adjust in order to perform dose adjustment, by initially adjusting each of the parameters, and determining the adjustment of which of the parameters leads to the lowest dose required for motor activation. The computer processor interprets this as indicating to which of the parameters the subject's neural system has greatest sensitivity, and varies the dose by adjusting this parameter.

For some applications, as an alternative to, or in addition to, the computer processor automatically determining that the subject is moving or attempting to move a limb upon which the electrodes are disposed, the subject may provide an input to the computer processor indicating that he/she is moving or attempting to move the limb. Similarly, as an alternative to, or in addition to, the computer processor automatically determining that the subject has finished moving or attempting to move the limb, the subject may provide an input to the computer processor indicating that he/she has finished moving or attempting to move the limb.

Some applications of the present invention relate to an electrical stimulation protocol that is delivered to a subject using electrodes, such as electrodes 22 of patch 20. The stimulation protocol is described hereinbelow with reference to FIGS. 7C-D. For some applications, using a stimulation protocol as described hereinbelow with reference to FIGS. 7C-D may reduce or even eliminate skin redness and/or irritation that is sometimes caused by transcutaneous electrical stimulation. For some applications, the stimulation protocol described hereinbelow with reference to FIGS. 7C-D is used for alternative or additional reasons.

Figure 7A:
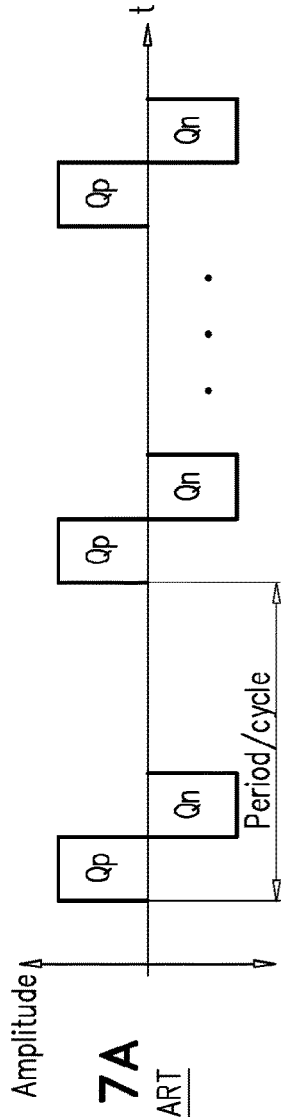
FIG. 7A is a graph showing an electrical stimulation protocol that is used in some prior art techniques.

Reference is now made to FIG. 7A, which is a graph showing an electrical stimulation protocol that is used in some prior art techniques. Nerve stimulation and/or modulation devices are based on harnessing electrical energy for addressing a medical condition. For example, transcutaneous electrical nerve stimulation ("TENS") is used to treat local pain, such as local lower-back pain. Typically, in such techniques, an electrical waveform is applied onto the subject's skin typically via a set of one (or more) pair of electrodes. Further typically, such waveforms are comprised of a cyclic, recurring set of electrical pulses, with each cycle having a positive phase and a negative phase, as shown in FIG. 7A.

Typically, a first one of the phases of such a waveform (e.g., the positive phase) is used to elicit the neuromodulation response, whereas the second phase (e.g., the negative phase) is provided in order to provide charge balancing. In theory, charge balancing is achieved by configuration the stimulation protocol such that the positive charge that is delivered to the subject's skin during the positive phase of each cycle (denoted 'Qp') is equal to the negative charge that is delivered to the subject's skin during the negative phase of each cycle (denoted 'Qn'). Thus, theoretically, over each cycle, and over the course of a stimulation session, the total amount of positive charge that is delivered to the subject's skin is equal to the total amount of negative charge that is delivered to the subject's skin, or, in other words, no residual charge exists on the subject's skin. (It is noted that in the context of the description of FIGS. 7A-7C, the terms positive charge and negative charge do not denote electrons and protons. Rather, an accumulation of positive charge denotes an accumulation of charge at a first one of the electrodes (e.g., the driving electrode), whereas an accumulation of negative charge denotes an accumulation of charge at the second electrode (e.g., the passive electrode), or vice versa.) Charge balance implies that there is no accumulation of charge at either one of the electrodes.

Figure 7B:
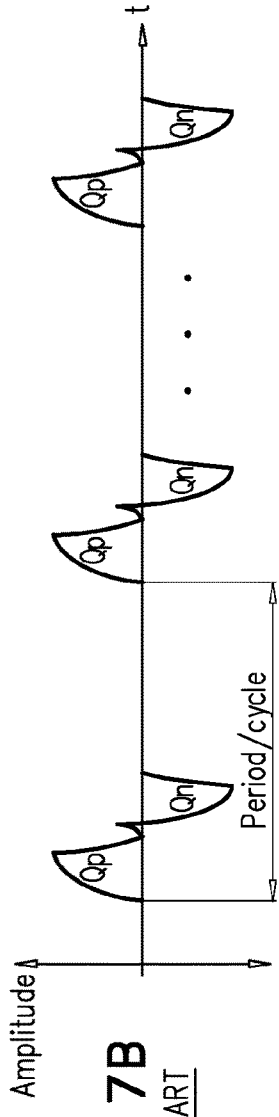
FIG. 7B is a graph showing how the prior art stimulation protocol shown in FIG. 7A may be delivered to a subject's skin under imperfect, real-life conditions.
Figure 7C:
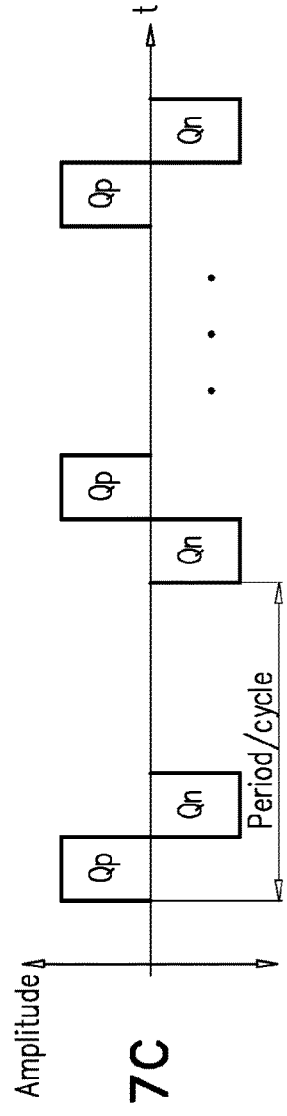
FIGS. 7C and 7D are graphs indicating a stimulation protocol that is delivered to a subject, in accordance with some applications of the present invention.
Figure 7D:
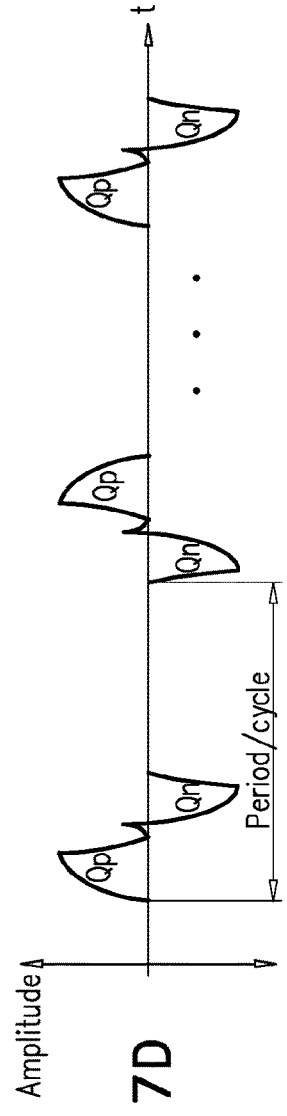

Reference is now made to FIG. 7B, which is a graph showing how the prior art stimulation protocol shown in FIG. 7A may be delivered to a subject's skin under imperfect, real-life conditions. In real-life conditions, it is typically the case that the shape of the stimulation curve that is delivered to the subject's skin does not follow the theoretical shape. For example, this may be as a result of the degree of coupling of respective electrodes to the subject's skin being different from each other. In the example shown in FIG. 7B, due to the imperfect, real-life conditions, the area under the positive portion of the curve in each stimulation cycle (which corresponds to positive charge, Qp) is greater than the area under the negative portion of the curve in each stimulation cycle (which corresponds to negative charge, Qn). In such cases, there is a gradual accumulation of charge on the subject's skin. In some cases, this can lead to irritation of the subject's skin, marks on the subject's skin, and/or other undesired effects. It is noted that such undesired effects are not limited to the particular stimulation protocol illustrated in FIG. 7A, or to the particular real-life stimulation curve shown in FIG. 7B. For example, in some cases such effects will occur even if the stimulation protocol is a sinusoidal curve rather than the square-wave curve shown in FIG. 7A. Similarly, such effects may occur if the area under the negative portion of the curve is greater than the area under the positive portion of the curve, such that there is an accumulation of negative charge on the subject's skin.

Reference is now made to FIGS. 7C-D, which are graphs indicating a stimulation protocol that is delivered to a subject, in accordance with some applications of the present invention. FIG. 7C shows the electrical stimulation protocol, and FIG. 7D shows how the stimulation protocol shown in FIG. 7C may be delivered to a subject's skin under imperfect, real-life conditions, such as explained above regarding the prior art stimulation protocol shown in FIG. 7B. As described hereinabove, the electrical stimulation is delivered by at least one computer processor in cycles, each cycle containing a first phase (e.g., a positive phase), which provides the neuromodulation signal, and a second phase (e.g., a negative phase), which is applied to provide charge balancing. Typically, after each set of N cycles (N being an integer), the roles of the electrodes belonging to the electrode pair that provides the electrical simulation are switched, such that the driving electrode becomes the passive electrode (i.e., sink electrode), and vice versa. In other words, every N cycles, a direction in which the current cycle (i.e., current flow) is driven between the first and second electrodes is reversed by the at least one computer processor, N being an integer. In other words, after each set of N cycles, the order in which the positive and negative phases of the cycle are delivered is reversed (the polarity of the phases illustrated in FIG. 7C-D is measured with reference to the first electrode). For example, as shown, in FIGS. 7C-D, N is equal to 1, such that after each cycle, the roles of the electrodes are switched in the above-described manner, and, for example, whereas in the first cycle the positive phase is applied prior to the negative phase being applied, in the second cycle, the negative phase is applied prior to the positive phase being applied. For some applications, N is any integer between 1 and 10, or any integer between 1 and 1000.

Thus, the at least one computer processor is configured to repeatedly reversing the direction in which the current cycle (i.e., current flow) is driven between the first and second electrodes. For some applications, rather than measure the repletion periods in in current cycles, as described above, the at least one computer processor is configured to repeatedly reverse the direction in which the current cycle is driven in repetition periods measured in units of time.

For some applications, each positive phase (i.e., portion) of at least some of the current cycles (e.g., of each of the current cycles) includes a plurality of pulses (e.g., two to 100, such as two to ten, e.g., two to five pulses), and/or each negative phase (i.e., portion) of the current cycles (e.g., of each of the current cycles) includes a plurality of pulses (e.g., two to 100, such as two to ten, e.g., two to five pulses) (configuration not shown in FIGS. 7C-D). For some applications, the interval between each of the pulses may equal the interval between the last of the positive pulses of the positive phase and the first of the pulses of the following negative phase of the same cycle (and, for the pulses of reversed direction, may equal the interval between the last of the negative pulses of the negative phase and the first of the pulses of the following positive phase of the same cycle). Alternatively, for some applications, the interval between each of the pulses may be less than the interval between the last of the positive pulses of the positive phase and the first of the pulses of the following negative phase of the same cycle (and, for the pulses of reversed direction, may be less than the interval between the last of the negative pulses of the negative phase and the first of the pulses of the following positive phase of the same cycle).

The inventors of the present application have found that providing electrical stimulation in the manner described with reference to FIGS. 7C-D, results in there being no irritation caused to the subject's skin, marks on the subject's skin, and/or other undesired effects. It is hypothesized that this is because by applying the electrical stimulation in the above-described manner, even if, for example, there is an accumulation of charge at the driving electrode, this charge is removed once the electrodes are reversed.

For some applications, the stimulation protocol described with respect to FIGS. 7C-D is applied in combination with other stimulation parameters and/or techniques described here.

Although some applications of the present invention are described as being performed using electrodes 22 disposed on patch 20, the scope of the present application includes applying electrical stimulation signals to a subject having signal characteristics as described herein, but via a different type of electrodes to those described hereinabove. For example, the stimulation may be applied via implanted electrodes, subcutaneous electrodes, and/or any other type of electrodes configured to electrically stimulate a subject.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 24. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage, and/or storage in a remote server is used.

A data processing system suitable for storing and/or executing program code will include at least one processor (e.g., computer processor 24) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that the methods described herein can be implemented by computer program instructions. These computer program instructions may be provided to a processor of a general-purpose computer, special purpose computer, or other programmable data processing apparatus to produce a machine, such that the instructions, which execute via the processor of the computer (e.g., computer processor 24) or other programmable data processing apparatus, create means for implementing the functions/acts specified in the methods described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the methods described in the present application. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the methods described in the present application.

Computer processor 24 and the other computer processors described herein are typically hardware devices programmed with computer program instructions to produce a special purpose computer. For example, when programmed to perform the methods described herein, the computer processor typically acts as a special purpose electrical-stimulation computer processor. Typically, the operations described herein that are performed by computer processors transform the physical state of a memory, which is a real physical article, to have a different magnetic polarity, electrical charge, or the like depending on the technology of the memory that is used.

In an embodiment, techniques and apparatus described in one or more of the following patent applications, which are assigned to the assignee of the present application and are incorporated herein by reference, are combined with techniques and apparatus described herein: US Patent Application Publication 2017/0368344 to Ironi et al.; PCT Publication WO 2017/122195 to Harpak et al.; US Patent Application Publication 2018/0345020 to Ironi et al.; PCT Publication WO 2018/060997 to Ironi et al.; PCT Publication WO 2018/215879 to Ironi; U.S. Provisional Application 62/401,380, filed Sep. 29, 2016; U.S. Provisional Application 62/401,392, filed Sep. 29, 2016; U.S. Provisional Application 62/412,981, filed Oct. 26, 2016; U.S. Provisional Application 62/614,613, filed Jan. 8, 2018; U.S. Provisional Application 62/616,029, filed Jan. 11, 2018; U.S. Provisional Application 62/636,306, filed Feb. 28, 2018

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
   a battery comprising first and second poles;
   a circuit board that comprises electronic circuitry, the second pole of the battery being electrically coupled to the electronic circuitry; and
   a battery-isolation tab removably disposed between the first pole and the electronic circuitry, the battery-isolation tab comprising:
      a non-conductive substrate configured to electrically isolate the first pole from the electronic circuitry, while the battery-isolation tab is disposed between the first pole and the electronic circuitry; and
      a conductive layer disposed upon the non-conductive substrate, the conductive layer being electrically coupled to the first pole of the battery and configured to facilitate electrical coupling of the first pole of the battery to the electronic circuitry, while the battery-isolation tab is disposed between the first pole and the electronic circuitry,
   wherein the apparatus is configured such that upon permanent removal of the battery-isolation tab from being disposed between the first pole and the electronic circuitry, the first pole of the battery is in electrical contact with the electronic circuitry of the circuit board,
   wherein the apparatus further comprises:
      skin-contacting electrodes configured to come into electrical contact with skin of a subject;
      a hydrogel layer underneath the skin-contacting electrodes, the hydrogel layer being configured to adhere the apparatus to the subject's skin;
      a liner covering the hydrogel layer;
      current-outputting electrodes disposed between the circuit board and the skin-contacting electrodes; and
      current-receiving electrodes disposed between the circuit board and the skin-contacting electrodes,
   wherein the circuit board is configured to test a connectivity of the skin-contacting electrodes, without driving any current through the hydrogel layer, by driving a test current into the skin-contacting electrodes via the current-outputting electrodes while the liner covers the hydrogel layer, and detecting that the outputted current is received by the current-receiving electrodes.

2. The apparatus according to claim 1, further comprising an electrical connecting element configured to electrically couple the conductive layer of the battery-isolation tab to the electronic circuitry, thereby electrically coupling the first pole of the battery to the electronic circuitry.

3. The apparatus according to claim 2,
   wherein the apparatus is configured such that the first pole of the battery is in electrical contact with the electronic circuitry of the circuit board via an electrical connection on the electronic circuitry, while the battery-isolation tab is not disposed between the first pole and the electronic circuitry, and wherein the electrical connecting element is configured to electrically couple the conductive layer of the battery-isolation tab to a test point on the electronic circuitry, the test point electrically coupled to the electrical connection.

4. The apparatus according to claim 1, wherein the conductive layer is an upper conductive layer disposed on at least a portion of a top surface of the non-conductive substrate, wherein the battery-isolation tab further comprises a lower conductive layer disposed on at least a portion of a bottom surface of the non-conductive substrate, such that the non-conductive substrate electrically isolates the upper conductive layer and the lower conductive layer from each other, wherein the lower conductive layer is electrically coupled to the electronic circuitry, while the battery-isolation tab is disposed between the first pole and the electronic circuitry, and wherein the upper and the lower conductive layers are together configured to facilitate electrical coupling of the first pole of the battery to the electronic circuitry, while the battery-isolation tab is disposed between the first pole and the electronic circuitry.

5. The apparatus according to claim 4, further comprising an electrical connecting element configured to electrically couple the upper conductive layer to the lower conductive layer, thereby electrically coupling the first pole of the battery to the electronic circuitry.

6. The apparatus according to claim 1, wherein the apparatus further comprises a battery housing configured to house the battery, such that the second pole of the battery is in contact with at least a portion of the electronic circuitry, the battery housing comprising:

mechanical connectors configured to mechanically connect the battery housing to the circuit board; and electrical connectors configured to electrically couple the second pole of the battery to the electronic circuitry, the mechanical connectors and the electrical connectors of the battery housing being coupled to each other, such that by virtue of the mechanical connectors connecting the battery housing to the circuit board, the electrical connectors electrically couple the second pole of the battery to the electronic circuitry.

7. The apparatus according to claim 6, wherein the circuit board is shaped to define slots, and wherein the mechanical connectors comprise protrusions that are configured to click into respective slots of the circuit board.

8. A method for manufacturing an apparatus, the method comprising:

assembling a battery, which includes first and second poles, with a circuit board that comprises electronic circuitry, such that (a) the second pole of the battery is electrically coupled to the electronic circuitry, and (b) a battery-isolation tab is removably disposed between the first pole and the electronic circuitry, such that a non-conductive substrate of the battery-isolation tab electrically isolates the first pole from the electronic circuitry;

while the battery-isolation tab is removably disposed between the first pole and the electronic circuitry, temporarily electrically coupling the first pole of the battery to the electronic circuitry via a conductive layer that is (a) disposed upon the non-conductive substrate of the battery-isolation tab and (b) electrically coupled to the first pole of the battery; and while the first pole of the battery is temporarily electrically coupled to the electronic circuitry, testing functionality of the electronic circuitry, wherein the apparatus is configured such that the first pole of the battery is in electrical contact with the electronic circuitry of the circuit board upon removal of the battery-isolation tab from between the first pole and the electronic circuitry after manufacturing of the apparatus, wherein the apparatus further comprises:

skin-contacting electrodes configured to come into electrical contact with skin of a subject;

a hydrogel layer underneath the skin-contacting electrodes, the hydrogel layer being configured to adhere the apparatus to the subject's skin;

a liner covering the hydrogel layer;

current-outputting electrodes disposed between the circuit board and the skin-contacting electrodes; and current-receiving electrodes disposed between the circuit board and the skin-contacting electrodes, wherein the method further comprises testing the connectivity of the skin-contacting electrodes, without driving any current through the hydrogel layer, by driving a test current into the skin-contacting electrodes via the current-outputting electrodes while the liner covers the hydrogel layer, and detecting that the outputted current is received by the current-receiving electrodes.

9. The method according to claim 8, wherein electrically coupling the first pole of the battery to the electronic circuitry comprises using an electrical connecting element to electrically couple the conductive layer of the battery-isolation tab to the electronic circuitry, thereby electrically coupling the first pole of the battery to the electronic circuitry.

10. The method according to claim 9, wherein the apparatus is configured such that the first pole of the battery is in electrical contact with the electronic circuitry of the circuit board via an electrical connection on the electronic circuitry, while the battery-isolation tab is not disposed between the first pole and the electronic circuitry, and wherein using the electrical connecting element to electrically couple the conductive layer of the battery-isolation tab to the electronic circuitry comprises using the electrical connecting element to electrically couple the conductive layer of the battery-isolation tab to a test point on the electronic circuitry, the test point electrically coupled to the electrical connection.

11. The method according to claim 8, wherein the conductive layer is an upper conductive layer disposed on at least a portion of a top surface of the non-conductive substrate, wherein the battery-isolation tab further includes a lower conductive layer disposed on at least a portion of a bottom surface of the non-conductive substrate, such that the non-conductive substrate electrically isolates the upper conductive layer and the lower conductive layer from each other, wherein the lower conductive layer is electrically coupled to the electronic circuitry, while the battery-isolation tab is disposed between the first pole and the electronic circuitry, and wherein temporarily electrically coupling the first pole of the battery to the electronic circuitry comprises wherein temporarily electrically coupling the first pole of the battery to the electronic circuitry via the upper and the lower conductive layers.

12. The method according to claim 11, wherein electrically coupling the first pole of the battery to the electronic circuitry comprises using an electrical connecting element to electrically couple the upper conductive layer to the lower conductive layer, thereby electrically coupling the first pole of the battery to the electronic circuitry.

13. The method according to claim 8,
wherein the apparatus further includes a battery housing configured to house the battery, such that the second pole of the battery is in contact with at least a portion of the electronic circuitry, the battery housing including:
mechanical connectors configured to mechanically connect the battery housing to the circuit board; and
electrical connectors configured to electrically couple the second pole of the battery to the electronic circuitry, and
wherein assembling the battery with the circuit board comprises coupling the mechanical connectors and the electrical connectors of the battery housing to each other, such that by virtue of the mechanical connectors connecting the battery housing to the circuit board, the electrical connectors electrically couple the second pole of the battery to the electronic circuitry.

14. The method according to claim 13, wherein the circuit board is shaped to define slots, wherein the mechanical connectors include protrusions, and wherein assembling the battery with the circuit board comprises clicking the protrusions into respective slots of the circuit board.

15. Apparatus for use with a power supply, the apparatus comprising:
a battery comprising first and second poles;
a circuit board that comprises electronic circuitry, the second pole of the battery being electrically coupled to the electronic circuitry; and
a battery-isolation tab removably disposed between the first pole and the electronic circuitry, the battery-isolation tab comprising:
a non-conductive substrate configured to electrically isolate the first pole from the electronic circuitry, while the battery-isolation tab is disposed between the first pole and the electronic circuitry;
a first conductive layer disposed upon the non-conductive substrate, the first conductive layer being electrically coupled to the electronic circuitry, while the battery-isolation tab is disposed between the first pole and the electronic circuitry;
a second conductive layer disposed upon the non-conductive substrate, the second conductive layer being electrically coupled to the second pole of the battery, while the battery-isolation tab is disposed between the first pole and the electronic circuitry,
wherein the first and the second conductive layers are electrically isolated from each other and are configured to facilitate electrical coupling of the power supply to the electronic circuitry, while the battery-isolation tab is disposed between the first pole and the electronic circuitry, and
wherein the apparatus is configured such that upon permanent removal of the battery-isolation tab from being disposed between the first pole and the electronic circuitry, the first pole of the battery is in electrical contact with the electronic circuitry of the circuit board,
wherein the apparatus further comprises:
skin-contacting electrodes configured to come into electrical contact with skin of a subject;
a hydrogel layer underneath the skin-contacting electrodes, the hydrogel layer being configured to adhere the apparatus to the subject's skin;
current-outputting electrodes disposed between the circuit board and the skin-contacting electrodes; and
current-receiving electrodes disposed between the circuit board and the skin-contacting electrodes,
wherein the circuit board is configured to test a connectivity of the skin-contacting electrodes, without driving any current through the hydrogel layer, by driving a test current into the skin-contacting electrodes via the current-outputting electrodes, and detecting that the outputted current is received by the current-receiving electrodes.

16. The apparatus according to claim 15, further comprising first and second leads, which are configured to electrically couple the first and the second conductive layers to respective poles of the power supply, thereby electrically coupling the power supply to the electronic circuitry.

17. A method for manufacturing an apparatus, the method comprising:
assembling a battery, which includes first and second poles, with a circuit board that comprises electronic circuitry, such that (a) the second pole of the battery is electrically coupled to the electronic circuitry, and (b) a battery-isolation tab is removably disposed between the first pole and the electronic circuitry, such that a non-conductive substrate of the battery-isolation tab electrically isolates the first pole from the electronic circuitry;
while the battery-isolation tab is removably disposed between the first pole and the electronic circuitry, temporarily electrically coupling a power supply, separate from the battery, to the electronic circuitry via (a) a first conductive layer disposed upon the non-conductive substrate, the first conductive layer being electrically coupled to the electronic circuitry, and (b) a second conductive layer disposed upon the non-conductive substrate, the second conductive layer being electrically coupled to the second pole of the battery, wherein the first and the second conductive layers are electrically isolated from each other; and
while the power supply is temporarily electrically coupled to the electronic circuitry, testing functionality of the electronic circuitry,
wherein the apparatus is configured such that the first pole of the battery is in electrical contact with the electronic circuitry of the circuit board upon removal of the battery-isolation tab from between the first pole and the electronic circuitry after manufacturing of the apparatus,
wherein the apparatus further comprises:
skin-contacting electrodes configured to come into electrical contact with skin of a subject;
a hydrogel layer underneath the skin-contacting electrodes, the hydrogel layer being configured to adhere the apparatus to the subject's skin;
current-outputting electrodes disposed between the circuit board and the skin-contacting electrodes; and
current-receiving electrodes disposed between the circuit board and the skin-contacting electrodes,
wherein the circuit board is configured to test a connectivity of the skin-contacting electrodes, without driving any current through the hydrogel layer, by driving a test current into the skin-contacting electrodes via the current-outputting electrodes, and detecting that the outputted current is received by the current-receiving electrodes.

18. The method according to claim 17, wherein electrically coupling the power supply to the electronic circuitry comprises using first and second leads to electrically couple the first and the second conductive layers to respective poles of the power supply, thereby electrically coupling the power supply to the electronic circuitry.

* * * * *